Figure 1:
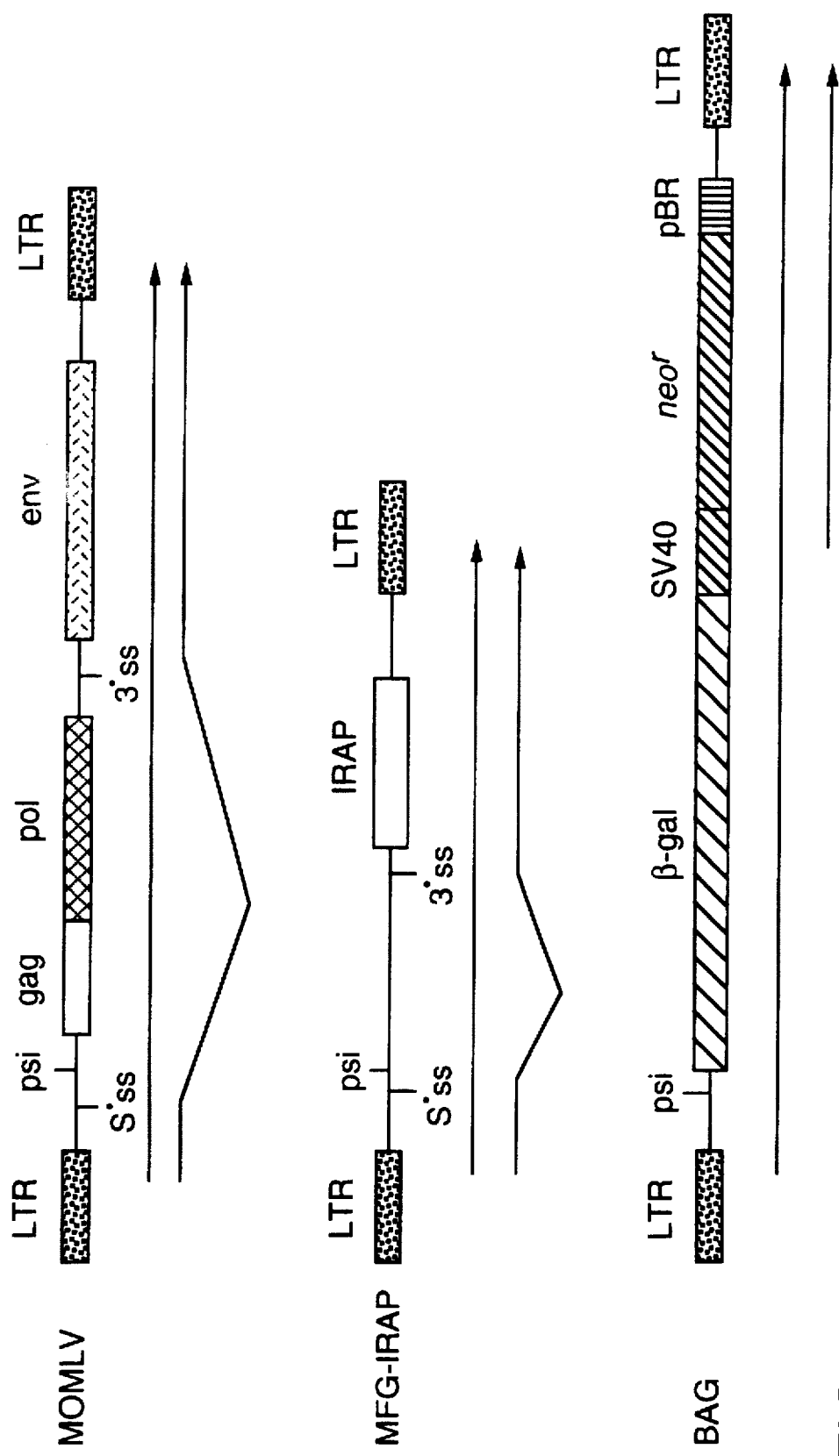

United States Patent [19]
Evans et al.

[11] Patent Number: 5,766,585
[45] Date of Patent: Jun. 16, 1998

[54] SYSTEMIC GENE TREATMENT OF CONNECTIVE TISSUE DISEASES WITH IRAP-1

[75] Inventors: Christopher H. Evans; Paul D. Robbins, both of Pittsburgh, Pa.

[73] Assignee: University of Pittsburgh of the Commonwealth System of Higher Education, Pittsburgh, Pa.

[21] Appl. No.: 697,180

[22] Filed: Aug. 20, 1996

Related U.S. Application Data

[63] Continuation of Ser. No. 167,642, Dec. 14, 1993, abandoned.

[51] Int. Cl.$^6$ .......................... A01N 43/04; A01N 63/00; C12N 5/16; C12N 15/07
[52] U.S. Cl. .................. 424/93.21; 424/93.1; 424/93.2; 424/529; 424/534; 435/172.3; 435/320.1; 514/44; 935/23; 935/71
[58] Field of Search .................................. 435/69.1, 70.1, 435/703, 172.1, 172.3, 320.1, 325; 424/93.1, 93.2, 93.21, 529, 534; 514/44; 935/22, 32, 34, 70, 71, 23

[56] References Cited

U.S. PATENT DOCUMENTS

| | | | |
|---|---|---|---|
| 5,081,228 | 1/1992 | Dower et al. | 530/35.1 |
| 5,180,812 | 1/1993 | Dower et al. | 530/351 |
| 5,319,071 | 6/1994 | Dower et al. | 530/350 |
| 5,334,380 | 8/1994 | Kilbourn et al. | 424/85.2 |
| 5,350,683 | 9/1994 | Sims et al. | 435/69.1 |
| 5,399,346 | 3/1995 | Anderson et al. | 424/93.21 |

FOREIGN PATENT DOCUMENTS 9207943  5/1992  WIPO.

OTHER PUBLICATIONS

Yang, 1992. Critical Reviews in Biochem. 12(4):335–356.
Mulligan, 1993. Science 260:926–931.
Nienhaus et al., 1991. Cancer 67(10):2700–2704.
Ohashi et al., 1992. Proc. Natl. Acad. Sci. USA. 89:11332–11336.
Weinblatt, 1992. Journal of Rheumatology. 19(Sup. 32):85–91.
Barr et al. 1991. Science 254:1507–1509.
Manthorpe et al. 1993. Human Gene Therapy 4:419–431.
Bandara, et al., 1992. Gene Transfer to Synoviocytes: Prospects for Gene Transfer of Arthritis. DNA Cell Biol. 11:227–231.
Bandara, et al., 1993. Intrarticular Expression of Biologically Active Interleukin 1–Receptor–Antagonist Protein by Ex Vivo Gene Transfer. PNA 90:10765–10768.
Arend, et al., 1991. Interleukin 1 Receptor Antagonist: A New Member of the Interleukin 1 Family. J. Clin. Invest. 88: 1445–1451.
Raz, et al., 1993. Systemic Immunological Effects of Cytokine Genes Injected into Skeletal Muscle. PNAS 90: 4523–4527.
Hannum, et al., 1990. Interleukin–1 Receptor Antagonist Activity of a Human Interleukin–1 Inhibitor. Nature 343: 336–340.

(List continued on next page.)

*Primary Examiner*—Brian R. Stanton
*Attorney, Agent, or Firm*—Diane R. Meyers; Eckert Seamans Cherin & Mellott, LLC

[57] ABSTRACT

The present invention relates to methods of therapeutic or prophylactic treatment of connective tissue diseases by systemic or local delivery of a nucleic acid sequence to a mammalian host. Expression of the nucleic acid sequence results in the systemic delivery of a biologically active protein or peptide which acts to antagonize inflammatory, hypertrophic and erosive phenomenon associated with connective tissue disease. Systemic delivery of such gene products results in sustained treatment of connective tissue diseases such as rheumatoid arthritis and systemic lupus erythematosus.

3 Claims, 2 Drawing Sheets

OTHER PUBLICATIONS

Eisenberg, et al., 1990, Primary Structure and Functional Expression from cDNA of a Human Interleukin–1 Receptor Antagonist, Nature 343: 341–346.

Carter, et al., 1990, Purification, Cloning, Expression and Biological Characterization of an Interleukin–1 Receptor Antagonist Protein, Nature 344: 633–638.

Dinarello and Thompson, 1991, Blocking IL–1: Interleukin–1 Receptor Antagonist In Vivo and In Vitro, Immunology Today 12 (11): 404–410.

Dinarello, et al., 1993, Anticytokine Strategies in the Treatment of the Systemic Inflammatory Response Syndrome, JAMA 269: 1829–1835.

Dia, et al., 1992, Gene Therapy via Primary Myoblasts: Long–term Expression of Factor IX Protein Following Transplantation In Vivo, PNAS 89: 10892–10895.

Vannier, et al., 1992, Coordinated Antiinflammatory Effects of Interleukin–4: Interleukin–4 Supresses Interleukin–1 Production But Up–Regulates Gene Expression and Synthesis of Interluekin 1 Receptor Antagonist, PNAS 89:4076–4080.

Ohashi, et al., 1992, Efficient Transfer and Sustained High Expression of the Human Glucocereborsisdase Gene in Mice and Their Functional Macrophages Following Transplantation of Bone Marrow Transduced by a Retroviral Vector, PNAS 89: 11332–11336.

Bandara, et al., 1992, Synovial Cell Transplants for Gene Transfer to Joints, Transplantatin Proceedings 24(6): 2966.

Wolff, et al., 1990, Direct Gene Transfer into Mouse Muscle In Vivo, Nature 247:1465–1468.

de Waal Malefyt, et al., 1991, IL–10 Inhibits Cytokine Synthesis by Human Monocytes: An Autoregulatory Role of IL–10 Produced by Monocytes, J. Exp. Med. 174:1209–1220.

Fiorentino, et al., 1991, IL–10 Inhibits Cytokine Production by Activated Macrphages, J. Immunology 147:3815–3822.

Bodgan, et al., 1991, Macrophage Deactivation by Interleukin 10, J. Exp. Med. 174: 1549–1555.

Englemann, et al., 1989, A Tumor Necrosis Factor–Binding Protein Purified to Homogeneity from Human Urine Protects Cells from Tumor Necrosis Factor Toxicity, J. Biol. Chem. 264: 11974–11980.

Gatanga, et al., 1990, Identification of TNF–LT Blocking Factors in the Serum and Ultrafiltrates of Human Cancer Patients, 1990, Lymphokine Res. 9(2): 225–229.

Fanslow, et al., Regulation of Alloreactivity In Vivo by a Soluble Form of the Interleukin 1 Receptor, Science 248: 739–742.

Dayer, et al., 1986, Human Recombinant Interluekin 1 Stimulates Collagenase and Prostoglandin $E_2$ Production by Human Synovial Cells, J. Clin. Invest. 77: 645–648.

Dayer, et al., 1985, Cachectin/Tumor Necrosis Factor Stimulates Collagenase and Prostoglandin $E_2$ Production by Human Synovial Cells and Dermal Fibroblasts, J. Exp. Med. 162: 2163–2168.

Docherty and Murphy, 1990, The Tissue Metalloproteinase Activity and the Inhibitor TIMP: A Study Using cDNAs and Recombinant Proteins, Ann. Rheum. Dis. 49: 469–479.

Iigo, et al., 1991, ICAM–1–Dependent Pathway is Critically Involved in the Pathogenesis of Adjuvant Arthritis in Rats, J. Immunol., 147: 4167–4171.

Streeter, et al., 1988, A Tissue–Specific Endothelial Cell Molecule Involved in Lymphocyte Homing, Nature 331: 41–46.

Denning, et al, 1989, Antibodies Against CD44, p. 80, Lymphocyte Homing Receptor Augment T Cell Activation Via the CD2 Pathway, FASEB J. 3: A785 (#3243).

Skaleric, et al., 1991, Inhibitors of Reactive Oxygen Intermediates Supress Bacterial Cell Wall–Induced Arthritis, J. Immunol. 147:2559–2564.

McQuillan, et al., 1986, Stimulation of Proteoglycan Biosynthesis by Serum and Insulin–like Growth Factor–1 in Cultured Bovine Articular Cartilage, Biochem. J. 240: 423–430.

Morales and Roberts, 1988, Transforming Growth Factor β Regulates the Metabolism of Proteoglycans in Bovine Cartilage Organ Cultures, J. Biol. Chem. 263: 12828–12831.

Ignotz and Massague, 1986, Transforming Growth Factor–β Stimulates the Expression of Fibronectin and Collagen and Their Incorporation Into the Extracellular Matrix, J. Biol. Chem. 261:4337–4345.

Ingontz and Massague, 1987, Cell Adhesion Protein Receptors as Targets for Transforming Growth Factor–β Action, Cell 51: 189–197.

Karlsson, et al., 1993, Gene Transfer and Bone Marrow Transplantation with Special Reference to Gaucher's Disease, Bone Marrow Transplantation 11: 124–127.

Miller, 1992, Retroviral Vectors, Current Topics in Microbiology and Immunology, 158: 1–24.

Anderson, et al., 1990, The ADA Human Gene Therapy Protocol, Human Gene Therapy 1: 331–362.

Essner, et al., 1989, IL–4 Down–Regulates IL–1 and TNF Gene Expression in Human Monocytes, J. Immunol. 142:3857–3861.

Balavoine, et al., 1986, Prostoglandin $E_2$ and Collogenase Production Production by Fibroblasts and Synovial Cells is Regulated by Urine–Derived Human Interleukin–1 and Inhibitors, J. Clin. Invest. 78: 1120–1124.

Danos and Mulligan, 1988, Safe and Efficient Generation of Recombinant Retroviruses With Amphotropic and Ecotropic Host Ranges, PNAS 85: 6460–6464.

Howard and O'Garra, 1992, Biological Properties of Interleukin–10, Immunology Today 13: 198–200.

Larrick, 1989, Native Interleukin 1 Inhibitors, Immunology Today 10(2): 61–66.

Bandara, et al., 1993, Gene Transfer to Synovium, 39th Annual Meeting, Orthopaedic Research Society, p. 242.

Galea–Lauri, et al., 1993, In Vivo Gene Transfer to Synovium Using Cationic Liopsomes, J. Cell. Biochem. Supp. 17E, 236 (#SZ307).

Galea–Lauri, et al. 1993. Intrarticular Expression at the Interleukin–1 Receptor Antagonist Protein by Ex–Vivo Gene Therapy. J. Cell Biochem. Supp. 17E, 224(SZ101).

Evans, et al., 1992, Gene Transfer to Joints for Arthritis Therapy, J. Cell. Biochem. Supp. 17E p. 46 (V207).

Bandara, et al., 1992, Intraarticular Expression of IRAP by Gene Transfer, Arthrit. & Rheum. 35(9): S193 (#C161).

Aderka, et al., 1993, Correlation Between Serum Levels of Soluable Tumor Necrosis Factor Receptor and Disease Activity in Systemic Lupus Erythematosus, Arthrit. & Rheum., pp. 1111–1120, (V36)(#8).

Anderka et al., 1993. Arthritis & Rheumatism 36(8):1111–1120.

Nabel, et al., 1990. Site–Specific Gene Expression in Vivo by Direct Gene Transfer Into Arterial Wall, pp. 1285–1288.

Deleuran, et al., 1992, Localization of Interleukin–1α, Type Interleukin–1 Receptor and Interleukin–1 Receptor Antagonist in the Synovial Membrane and Cartilage/Pannus Junction in Rheumatoid Arthritis, British Society for Rheum., pp. 801–809.

Koch, et al., 1992, Expression of Interleukin–1 and Interleukin–1 Receptor Antagonist by Human Rheumatoid Synovial Tissue Macrophages, pp. 23–29 (V65) (#1).

Conti, et al., 1992, Inhibition of Interleukin–1β mRNA Expression and Interleukin–1æ and β Secretion by a Specific Human Recombinant Interleukin–1 Receptor Antagonist in Human Peripheral Blood Mononuclear Cells, Immunology, pp. 245–250.

Hung, et al., 1993, Inarticular Expression of IRAP by Gene Transfer: Inhibition of IL–Induced Pathology, Rheum., pp. S46 (V36).

Malyak, et al., 1993, Levels of Synovial Fluid Interleukin–1 Receptor Antagonist in Rheumatoid Arthritis and other Arthropathies, pp. 781–789, Arthrit and Rheum. (V36) (#6).

Firestein, et al., 1992, IL–1 Receptor Antagonist Protein Production and Gene Expression in Rheumatoid Arthritis and Osteoarthritis Synovium, The Journ. of Immunology, pp. 1054–1062, (V149) (#3).

Roessier, et al., 1993, Adenoviral–medicated Gene Transfer to Rabbit Synovium in Vivo, J. Clin. Invest., pp. 1085–1092 (V92).

McColl, et al., 1992, Human Neutrophils Produce High Levels of the Interleukin 1 Receptor Antagonist in Response to Granulocyte/Macrophage Colony–Stimulating Factor and Tumor Necrosis Factor æ, J. Exp. Med. pp. 593–598 (V176).

Arend, 1993 Interleukin–1 Receptor Antagonist, Advances in Immunology pp. 167–227, (V54).

Heilig, et al., 1993, Evaluation of Soluble Tumor Necrosis Factor (TNF) Receptors and TNF Receptor Antibodies in Patients with Systemic Lupus Erythematodes, Progressive Systemic Sclerosis and Mixed Connective Tissue Disease, Journ. Clin. Immunology, pp. 321–328, (V13) (#5).

Lombard, et al., 1993, Soluble Tumor Necrosis Factor Receptors in Human Inflammatory Synovial Fluids, Arthrit. and Rheum. pp. 485–489 (V36) (#4).

Smolen, et al., 1993, Tumour Necrosis Factor (TNF) and Soluble TNF Receptor (TNF-R) In Rheumatic Diseases, J. Immunology, p. 298A (V150) (Part 2).

| | |
|---|---:|
| AAGCTTCCGA CAGA ATG GAA ATC TGC AGA GGC CTC CGC AGT CAC CTA ATC<br>      Met Glu Ile Cys Arg Gly Leu Arg Ser His Leu Ile<br>       1      5        10 | 50 |
| ACT CTC CTC CTC TTC CTG TTC CAT TCA GAG ACG ATC TGC CGA CCC TCT<br>Thr Leu Leu Leu Phe Leu Phe His Ser Glu Thr Ile Cys Arg Pro Ser<br>    15       20        25 | 98 |
| GGG AGA AAA TCC AGC AAG ATG CAA GCC TTC AGA ATC TGG GAT GTT AAC<br>Gly Arg Lys Ser Ser Lys Met Gln Ala Phe Arg Ile Trp Asp Val Asn<br>   30       35       40 | 146 |
| CAG AAG ACC TTC TAT CTG AGG AAC AAC CAA CTA GTT GCT GGA TAC TTG<br>Gln Lys Thr Phe Tyr Leu Arg Asn Asn Gln Leu Val Ala Gly Tyr Leu<br>45       50       55       60 | 194 |
| CAA GGA CCA AAT GTC AAT TTA GAA GAA AAG ATA GAT GTG GTA CCC ATT<br>Gln Gly Pro Asn Val Asn Leu Glu Glu Lys Ile Asp Val Val Pro Ile<br>      65       70       75 | 242 |
| GAG CCT CAT GCT CTG TTC TTG GGA ATC CAT GGA GGG AAG ATG TGC CTG<br>Glu Pro His Ala Leu Phe Leu Gly Ile His Gly Gly Lys Met Cys Leu<br>    80       85        90 | 290 |
| TCC TGT CTC AAG TCT GGT GAT GAG ACC AGA CTC CAG CTG GAG GCA GTT<br>Ser Cys Val Lys Ser Gly Asp Glu Thr Arg Leu Gln Leu Glu Ala Val<br>   95       100      105 | 338 |
| AAC ATC ACT GAC CTG AGC GAG AAC AGA AAG CAG GAC AAG CGC TTC GCC<br>Asn Ile Thr Asp Leu Ser Glu Asn Arg Lys Gln Asp Lys Arg Phe Ala<br> 110      115       120 | 386 |
| TTC ATC CGC TCA GAC AGT GGC CCC ACC ACC AGT TTT GAG TCT GCC GCC<br>Phe Ile Arg Ser Asp Ser Gly Pro Thr Thr Ser Phe Glu Ser Ala Ala<br>125      130       135      140 | 434 |
| TGC CCC GGT TGG TTC CTC TGC ACA GCG ATG GAA GCT GAC CAG CCC GTC<br>Cys Pro Gly Trp Phe Leu Cyc Thr Ala Met Glu Ala Asp Gln Pro Val<br>      145      150       155 | 482 |
| AGC CTC ACC AAT ATG CCT GAC GAA GGC GTC ATG GTC ACC AAA TTC TAC<br>Ser Leu Thr Asn Met Pro Asp Glu Gly Val Met Val Thr Lys Phe Tyr<br>      160      165      170 | 530 |
| TTC CAG GAG GAC GAG TAGTACTGCC CAGGCCTGCC TGTTCCCATT CTTGCATGAA<br>Phe Gln Glu Asp Glu<br>      175 | 585 |
| GCTT | 589 |

FIG. 2

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:1:

```
CATGGAAATC TGCA                                                         14
```

( 2 ) INFORMATION FOR SEQ ID NO:2:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:2:

```
GATTTC                                                                   6
```

( 2 ) INFORMATION FOR SEQ ID NO:3:

( i ) SEQUENCE CHARACTERISTICS:
        ( A ) LENGTH: 589 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( G ) CELL TYPE: Human Monocyte
        ( H ) CELL LINE: U937

( v i i ) IMMEDIATE SOURCE:
        ( A ) LIBRARY: Clontech (HL1036a)
        ( B ) CLONE: Human IRAP ( i x ) FEATURE:
        ( A ) NAME/KEY: CDS
        ( B ) LOCATION: 15..548

( x i ) SEQUENCE DESCRIPTION: SEQ ID NO:3:

```
AAGCTTCCGA CAGA ATG GAA ATC TGC AGA GGC CTC CGC AGT CAC CTA ATC          50
              Met Glu Ile Cys Arg Gly Leu Arg Ser His Leu Ile
               1               5                      10

ACT CTC CTC CTC TTC CTG TTC CAT TCA GAG ACG ATC TGC CGA CCC TCT          98
Thr Leu Leu Leu Phe Leu Phe His Ser Glu Thr Ile Cys Arg Pro Ser
            15                  20                  25

GGG AGA AAA TCC AGC AAG ATG CAA GCC TTC AGA ATC TGG GAT GTT AAC         146
Gly Arg Lys Ser Ser Lys Met Gln Ala Phe Arg Ile Trp Asp Val Asn
        30                  35                  40

CAG AAG ACC TTC TAT CTG AGG AAC AAC CAA CTA GTT GCT GGA TAC TTG         194
Gln Lys Thr Phe Tyr Leu Arg Asn Asn Gln Leu Val Ala Gly Tyr Leu
 45                  50                  55                  60

CAA GGA CCA AAT GTC AAT TTA GAA GAA AAG ATA GAT GTG GTA CCC ATT         242
Gln Gly Pro Asn Val Asn Leu Glu Glu Lys Ile Asp Val Val Pro Ile
```

-continued

|  |  |  | 65 |  |  |  |  | 70 |  |  |  |  | 75 |  |  |  |
|---|---|---|---|---|---|---|---|---|---|---|---|---|---|---|---|---|
| GAG | CCT | CAT | GCT | CTG | TTC | TTG | GGA | ATC | CAT | GGA | GGG | AAG | ATG | TGC | CTG | 290 |
| Glu | Pro | His | Ala | Leu | Phe | Leu | Gly | Ile | His | Gly | Gly | Lys | Met | Cys | Leu |  |
|  |  |  | 80 |  |  |  |  | 85 |  |  |  |  | 90 |  |  |  |
| TCC | TGT | GTC | AAG | TCT | GGT | GAT | GAG | ACC | AGA | CTC | CAG | CTG | GAG | GCA | GTT | 338 |
| Ser | Cys | Val | Lys | Ser | Gly | Asp | Glu | Thr | Arg | Leu | Gln | Leu | Glu | Ala | Val |  |
|  |  | 95 |  |  |  |  | 100 |  |  |  |  | 105 |  |  |  |  |
| AAC | ATC | ACT | GAC | CTG | AGC | GAG | AAC | AGA | AAG | CAG | GAC | AAG | CGC | TTC | GCC | 386 |
| Asn | Ile | Thr | Asp | Leu | Ser | Glu | Asn | Arg | Lys | Gln | Asp | Lys | Arg | Phe | Ala |  |
|  | 110 |  |  |  |  | 115 |  |  |  |  | 120 |  |  |  |  |  |
| TTC | ATC | CGC | TCA | GAC | AGT | GGC | CCC | ACC | ACC | AGT | TTT | GAG | TCT | GCC | GCC | 434 |
| Phe | Ile | Arg | Ser | Asp | Ser | Gly | Pro | Thr | Thr | Ser | Phe | Glu | Ser | Ala | Ala |  |
| 125 |  |  |  |  | 130 |  |  |  |  | 135 |  |  |  |  | 140 |  |
| TGC | CCC | GGT | TGG | TTC | CTC | TGC | ACA | GCG | ATG | GAA | GCT | GAC | CAG | CCC | GTC | 482 |
| Cys | Pro | Gly | Trp | Phe | Leu | Cys | Thr | Ala | Met | Glu | Ala | Asp | Gln | Pro | Val |  |
|  |  |  |  | 145 |  |  |  |  | 150 |  |  |  |  | 155 |  |  |
| AGC | CTC | ACC | AAT | ATG | CCT | GAC | GAA | GGC | GTC | ATG | GTC | ACC | AAA | TTC | TAC | 530 |
| Ser | Leu | Thr | Asn | Met | Pro | Asp | Glu | Gly | Val | Met | Val | Thr | Lys | Phe | Tyr |  |
|  |  |  | 160 |  |  |  |  | 165 |  |  |  |  | 170 |  |  |  |
| TTC | CAG | GAG | GAC | GAG | TAGTACTGCC | CAGGCCTGCC | TGTTCCATT | CTTGCATGAA |  |  |  |  |  |  |  | 585 |
| Phe | Gln | Glu | Asp | Glu |  |  |  |  |  |  |  |  |  |  |  |  |
|  |  | 175 |  |  |  |  |  |  |  |  |  |  |  |  |  |  |

GCTT                                                                                                      589

( 2 ) INFORMATION FOR SEQ ID NO:4:

( i ) SEQUENCE CHARACTERISTICS:
        ( A ) LENGTH: 177 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Glu | Ile | Cys | Arg | Gly | Leu | Arg | Ser | His | Leu | Ile | Thr | Leu | Leu | Leu |
|---|---|---|---|---|---|---|---|---|---|---|---|---|---|---|---|
| 1 |  |  |  | 5 |  |  |  |  | 10 |  |  |  |  | 15 |  |
| Phe | Leu | Phe | His | Ser | Glu | Thr | Ile | Cys | Arg | Pro | Ser | Gly | Arg | Lys | Ser |
|  |  |  | 20 |  |  |  |  | 25 |  |  |  |  | 30 |  |  |
| Ser | Lys | Met | Gln | Ala | Phe | Arg | Ile | Trp | Asp | Val | Asn | Gln | Lys | Thr | Phe |
|  |  | 35 |  |  |  |  | 40 |  |  |  |  | 45 |  |  |  |
| Tyr | Leu | Arg | Asn | Asn | Gln | Leu | Val | Ala | Gly | Tyr | Leu | Gln | Gly | Pro | Asn |
|  | 50 |  |  |  |  | 55 |  |  |  |  | 60 |  |  |  |  |
| Val | Asn | Leu | Glu | Glu | Lys | Ile | Asp | Val | Val | Pro | Ile | Glu | Pro | His | Ala |
| 65 |  |  |  |  | 70 |  |  |  |  | 75 |  |  |  |  | 80 |
| Leu | Phe | Leu | Gly | Ile | His | Gly | Gly | Lys | Met | Cys | Leu | Ser | Cys | Val | Lys |
|  |  |  |  | 85 |  |  |  |  | 90 |  |  |  |  | 95 |  |
| Ser | Gly | Asp | Glu | Thr | Arg | Leu | Gln | Leu | Glu | Ala | Val | Asn | Ile | Thr | Asp |
|  |  |  | 100 |  |  |  |  | 105 |  |  |  |  | 110 |  |  |
| Leu | Ser | Glu | Asn | Arg | Lys | Gln | Asp | Lys | Arg | Phe | Ala | Phe | Ile | Arg | Ser |
|  |  | 115 |  |  |  |  | 120 |  |  |  |  | 125 |  |  |  |
| Asp | Ser | Gly | Pro | Thr | Thr | Ser | Phe | Glu | Ser | Ala | Ala | Cys | Pro | Gly | Trp |
|  | 130 |  |  |  |  | 135 |  |  |  |  | 140 |  |  |  |  |
| Phe | Leu | Cys | Thr | Ala | Met | Glu | Ala | Asp | Gln | Pro | Val | Ser | Leu | Thr | Asn |
| 145 |  |  |  |  | 150 |  |  |  |  | 155 |  |  |  |  | 160 |
| Met | Pro | Asp | Glu | Gly | Val | Met | Val | Thr | Lys | Phe | Tyr | Phe | Gln | Glu | Asp |
|  |  |  |  | 165 |  |  |  |  | 170 |  |  |  |  | 175 |  |

Glu

SYSTEMIC GENE TREATMENT OF CONNECTIVE TISSUE DISEASES WITH IRAP-1

This application is a continuation of application Ser. No. 08/167,642, filed Dec. 14, 1993, now abandoned.

1. INTRODUCTION

Gene therapy of certain connective tissue diseases would require delivery of a gene product to various sites, depending upon the disease, to promote comprehensive therapeutic coverage and the potential for prolonged availability throughout the patient. The present invention discloses methods of treating diseases or disorders comprising local or systemic delivery of a nucleic acid sequence which expresses a therapeutic or prophylactic gene product such that the expressed gene product is systemically delivered throughout the patient and available for prolonged periods.

2. BACKGROUND OF THE INVENTION

There are two main contexts in which genes or DNA sequences encoding a portion of that gene may be used in a therapeutic or prophylactic manner. The first is to compensate for heritable defects in the genome of the patient which lead to such diseases as Gaucher disease, hemophilia, and osteogenesis imperfecta. In the second context, genes are transferred for therapeutic reasons to individuals who may well be genetically normal. In this case, gene transfer is used as a drug delivery system for the protein(s), antisense RNA, ribozymes or a biologically active fragment thereof encoded by the transferred DNA sequence.

For example, treating arthritis locally with gene therapy based techniques has been described. Although arthritis is not, for the most part, a genetic disease, it has been shown to be a good candidate for gene treatment. Both in vivo and ex vivo gene therapy techniques for local treatment of joint disease protocols have been forwarded (see Bandara, et al., 1992, DNA Cell Biol. 11: 227-231). The transfer of a potentially therapeutic gene to a joint for treatment of inflammation and cartilage destruction associated with arthritis has been accomplished (U.S. application Ser. No. 027,750, by Glorioso, et al., filed Mar. 8, 1993).

Gene therapy in its barest sense addresses the chronicity of diseases such as arthritis, which can endure for the lifetime of the patient. Unlike traditional methods of drug delivery, gene therapy allows for the potential of a permanence of therapeutic effect to match the persistence of the disease. Furthermore, so far as antisense RNA, ribozymes and protein or biologically active fragments thereof are concerned, there are likely to be cost advantages. A DNA sequence should be inherently less expensive than its cognate gene product since it can be expressed many millions of times into the gene product.

Interleukin-1(IL-1) is now known to play a role in numerous diseases and disorders, in particular disorders accompanied by inflammation. IL-1 is a growth factor for synoviocytes and promotes their synthesis of matrix, two properties suggesting the involvement of IL-1 in the synovial hypertrophy that accompanies arthritis. IL-1 both enhances cartilaginous matrix breakdown and inhibits cartilaginous matrix synthesis by chondrocytes, thereby causing loss of cartilage while inhibiting its repair. IL-1 also induces bone resorption and thus may be involved in the loss of bone density seen in rheumatoid arthritis. IL-1 is inflammatory, serves as a growth factor for lymphocytes, is a chemotactic factor and a possible activator of polymorphonuclear leukocytes (PMNs). When present in a sufficient concentration, interleukin-1 may cause fever, muscle wasting and sleepiness. This being so, agents which antagonize the specific biological activity that IL-1 imparts during the course of that disorder might have therapeutic potential.

Although biological preparations have been disclosed that are able to block one or more of the actions of IL-1 (Larrick, 1989, Immunol. Today 10: 61–66), there are few instances in which an active principle has been purified to homogeneity and characterized, a prerequisite for any pharmacologic use of such an antagonist. Arend, et al. (1991, J. Clin. Invest. 88: 1445–1451) noted an IL-1 inhibitory activity in culture medium conditioned by macrophages. Balavoine, et al. (1986, J. Clin. Invest. 78: 1120–1124) found a similar activity in the urine of febrile patients. Subsequent studies showed these activities to result from the same protein which acted as a competitive inhibitor of the binding of IL-1 to its receptor. The gene encoding this antagonist of IL-1 has since been described (Hannum, et al., 1990, Nature 343: 336–340; Eisenberg, et al., 1990, Nature 343: 341–346; designated the IL-1 receptor antagonist [IL-1ra]; and Carter, et al., 1990, Nature 344: 633–638; designated the IL-1 receptor antagonist protein [IRAP]).

IL-1ra (hereinafter referred to as "IRAP") was originally identified as a product of activated macrophages. Additional cell types have been shown to synthesize this molecule; including synoviocytes, keratinocytes, chondrocytes and polymorphonuclear leukocytes. IRAP production is increased by a variety of cytokines and other stimuli, including IL-1, interleukin-3(IL-3), interleukin-4(IL-4), interleukin-10(IL-10) and tumor necrosis factor α(TNF-α). Several of these cytokines are generally considered to be pro-inflammatory. IRAP is only a weak inhibitor of the biological activities of IL-1. This reflects the ability of IL-1 to provoke a biological response in sensitive cells when only a few percent of its receptors are occupied. As the affinity of IRAP for these receptors does not exceed that of IL-1, the antagonist needs to be present at a molar excess of 10–1,000 fold to reduce responses to IL-1 by 50%. This may be a considerable impediment to the pharmacologic use of IRAP.

IRAP inhibits cellular responses to IL-1 under in vitro conditions, including induction of matrix metalloproteinases, induction of nitric oxide synthase, increased prostaglandin synthesis, cartilage degradation, bone resorption, increased expression of endothelial cell adhesion proteins, induction of interleukin-6(IL-6), TNF-α, and other cytokines, and cell division.

IRAP inhibits cellular responses to IL-1 under in vivo conditions, including increased IL-6, death in adrenalectomized animals, hypotension, fever, slow-wave sleep, cartilage breakdown, joint inflammation, hypoglycemia, acute phase response and increased corticosterone. In addition, IRAP may have potential therapeutic properties in a number of animal models of disease (for a review, see Dinarello and Thompson, 1991, Immunol. Today 12: 404–410). In vivo administration of IRAP is well tolerated. Normal animals, including humans, can be infused intravenously with high doses of this protein without any change in physiological or metabolic parameters. For example, human volunteers infused with 133 mg/h IL-1ra for 72 hours exhibited no change in clinical or laboratory values (Dinarello, et al., 1993, J. Amer. Med. Assoc. 269: 1829–1835).

IL-4 is a 20 kDa glycoprotein produced from T-lymphocytes. This cytokine binds to receptors on hematopoietic stem cells, B and T lymphocytes, mast cells and macrophages. Interleukin-4 also induces IgE production and B-cell surface antigens. Essner, et al. (1989, J. Immunol. 142: 3857–3861) determined that IL-4 down-regulates IL-1 and TNF-α at the level of mRNA transcription. Vannier, et al. (1992, Proc. Natl. Acad. Sci. USA 89: 4076–4080) confirmed the down-regulation of IL-1 by IL-4. Additionally, IL-4 was shown to up-regulate IRAP.

Raz, et al. (1993, Proc. Natl. Acad. Sci. USA 90:4523–4527) injected mice intramuscularly with a DNA plasmid encoding IL-4. Total IgG levels increased and a delayed-type hypersensitivity reaction to an antigen challenge was decreased. The systemic in vivo effects were consistent with a proposed role of IL-4 in stimulating the $T_H2$ lymphocyte subset-mediated immune response. The study also disclosed intramuscular injection and in vivo expression of IL-2 and TGF-1. However, the study did not monitor the possible regulatory effect of intramuscular injection and in vivo expression of the IL-4 gene on IL-1 or IRAP activity.

IL-10 is a 35–40 kDa acid sensitive cytokine produced by helper T-cells, B-cells, monocytes and macrophages. IL-10 has been shown to possess immunosuppressive properties in vitro, as indicated by an ability to suppress cytokine production and antigen specific proliferation of cultured clones of $T_H1$ cell when activated in an accessory cell-dependent manner (for a review, see Howard and O'Garra, 1992, Immunol. Today 13(6):198–200). IL-10, in a similar fashion as seen with IL-4, inhibits macrophage/monocyte production of IL-1β, IL-6, IL-8, GM-CSF, G-CSF and TNF-α and upregulates IRAP (de Waal Malefyt, et al., 1991, J. Exp. Med. 174: 1209–1220; Fiorentino, et al., 1991, J. Immunol. 147: 3815–3822; Bogdan, et al., 1991, J. Exp. Med. 174: 1549–1555).

Tumor necrosis factor - alpha (TNF-α) is a cytokine produced primarily by activated macrophages or lymphocytes. This cytokine is involved in numerous biological phenomena such as inflammation, endotoxic shock, anti-tumor and anti-viral activities. Soluble TNF-α binding proteins have been identified in normal human urine (Englemann, et al., 1989, J. Biol. Chem. 264: 11974–11980) and in serum of cancer patients (Gatanga, et al., 1990, Lymphokine Res. 9: 225–229).

Both the TNF-α and IL-1 soluble receptors inhibit receptor binding and biological activity of their respective cytokine in vitro. However, their in vivo role remains unclear. Fanslow, et al. (1990, Science 248: 739–742) disclose that direct administration of IL-1 soluble receptor prolongs allograft survival in mice. No mention is made regarding an ability to mount a prolonged biological response to the causal agent(s) of connective tissue disorders.

Connective tissue cells in monolayer culture produce low or undetectable levels of collagenase and other tissue metalloproteinases, such as stromelysin and gelatinase. However, high levels of these proteinases can be expressed in the presence of IL-1(Dayer, et al., 1986, J. Clin. Invest. 77: 645–648) and TNF-α(Dayer, et al., 1985, J. Exp. Med. 162: 2163–2168). Evidence indicates that these proteins promote degradation of extracellular matrix constituents associated with osteoarthritis and rheumatoid arthritis. Collagenase, stromelysin, and gelatinase are inhibited by the protein TIMP ("Tissue Inhibitor of MetalloProteinases"). The mechanism of TIMP inhibition of these metalloproteinases is not fully understood (see Docherty and Murphy, 1990, Ann. Rheum. Dis. 49: 469–479). There are two distinct TIMP genes encoding TIMP-1 and TIMP-2.

Leukocyte infiltration during an inflammatory response includes margination of these cells within microvessels, followed by adhesion to the vascular endothelial cells. Increases in leukocyte adhesion during inflammation involves specific interactions between cell surface adhesion molecules on both the leukocyte and endothelium cell surface. Examples of endothelium cell surface adhesion molecules are ICAM-1 and ELAM-1. Synthesis of both ICAM-1 and ELAM-1 are stimulated by IL-1. ICAM-1 is a receptor for the leukocyte adhesion protein, LFA-1. Anti-ICAM-1 antibodies have been shown to suppress pathogenesis of adjuvant arthritis in rats via inhibition of cell to cell adhesion (Iigo, et al., 1991, J. Immunol. 147: 4167–4171). Additional leukocyte localized proteins include CR3 and CR4 (which bind the complement degradation product C3bi). LFA-1, CR3 and CR4 are heterodimer integrin receptor proteins which possess the same β polypeptide, designated CD18. Additionally, CD44, which acts both as a lymphocyte homing receptor and as a receptor for certain matrix macromolecules such as glycosaminoglycan hyaluronic acid as well as certain types of collagen, mediates leukocyte binding to endothelial cells (Streeter, et. al., 1988, Nature, 331: 41–46). CD44 also up-regulates IL-1 production (Denning, et al., 1989FASEB J. 3: A765).

Reactive oxygen intermediates (ROI's) formed in response to inflammatory signals have been implicated in the destruction of extracellular matrix components such as hyaluronic acid and the proteoglycans collagen and elastin. The collagens are composed of a family of fibrous proteins which are secreted by connective tissue cells. Collagen is the major protein of the extracellular matrix. Elastin, also an extracellular matrix protein expressed in connective tissue cells, forms a cross-linked network possessing both elasticity and tensile strength. Skaleric, et al. (1991, J. Immunol. 147: 2559–2564) suggests that interaction of potential ROI inhibitors such as superoxide dismutase during an inflammatory episode may reduce the erosive effects of ROI's in connective tissue disorders.

Cartilage is comprised of chondrocytes embedded within an extensive extracellular matrix consisting primarily of collagen fibrils and various proteoglycans. Pathogenesis of connective tissue diseases such as arthritis includes erosion of proteoglycans. Two cartilage growth factors, insulin-like growth factor—1(IGF-1) and transforming growth factor-β (TGF-β) positively regulate proteoglycan synthesis (McQuillan, et al., 1986, Biochem. J. 240: 423–430; Morales and Roberts, 1989J. Biol. Chem. 263: 12828–12831). Additionally, TGF-β has been shown to regulate expression of adhesion molecules such as fibronectin and fibronectin receptors (Ignotz and Massague, 1986, J. Biol. Chem. 261: 4337–4345; Ignotz and Massague, 1987, Cell 51: 189–197).

Autoimmune diseases are characterized by an immune reaction against self antigens. In other words, the stricken individual has lost immunologic self-tolerance. Autoimmune antibodies may act against a single cell or organ, such as seen in Hashimoto's thyroiditis. Conversely, systemic autoimmune diseases such as rheumatoid arthritis (RA) and systemic lupus erythematosus (SLE) result in exposure and activity of autoimmune antibodies at multiple sites within the patient.

Mechanisms of autoimmune disease are thought to involve any one of a number, or combination thereof, of immunologic phenomenon which include, (1) bypass of T-helper cell function, (2) cross reaction with infectious agents, (3) direct activation of B-cells, (4) idiotype bypass mechanisms, and (5) imbalance of T-suppressor-helper function.

A number of systemic autoimmune and non-autoimmune diseases involving pathogenesis of connective tissue promote inflammation, cytokine mediation and tissue destruction. Therefore, it would be extremely useful to be able to employ antagonists of specific mediators of these processes so as to therapeutically or prophylactically treat these disorders.

Although proteins can be infused into patients during acute conditions, they are difficult to deliver as drugs in chronic diseases. It is difficult to promote a sustained therapeutic response via administration of a protein. Because the oral and transdermal routes are unavailable, proteins need to be delivered by injection. In view of their short systemic half-life, most need to be administered at frequent intervals. Another difficulty in treating a systemic disease is a requirement that the therapeutic or prophylactic antagonist be delivered to multiple sites within the patient, in contrast to local treatment of diseases such as arthritis. Therefore, it would be extremely useful to not only apply antagonists of respective systemic connective tissue disease mediators to patients, but to do so in a fashion which promotes multiple delivery sites and prolonged availability of the antagonist within the patient.

3. SUMMARY OF THE INVENTION

The present invention relates to methods of gene treatment of connective tissue disease which require systemic delivery within a mammalian host of a therapeutic or prophylactic protein, RNA, ribozyme or any biologically active fragment thereof. Systemic delivery (i.e., delivery to multiple sites within the patient) of the gene product may involve either systemic or local application of the nucleic acid sequence encoding the therapeutic or prophylactic gene product or biologically active fragment thereof. Viral or non-viral mediated delivery and sustained in vivo expression of the nucleic acid sequence of interest followed by systemic transport of the respective gene product results in a perpetuating systemic drug delivery system within the patient. The present invention discloses strategies providing for nucleic acids which encode therapeutic or prophylactic gene products or biologically active fragments for the treatment of connective tissue diseases and the insertion of these nucleic acid sequences into a viral or non-viral vector molecule via recombinant DNA techniques. Therefore, the present invention also discloses various recombinant vectors for use in systemic treatment of connective tissue diseases or disorders.

3.1. CONNECTIVE TISSUE DISEASES TREATED BY SYSTEMIC DELIVERY OF THERAPEUTIC OR PROPHYLACTIC GENE PRODUCTS

The present invention discloses methods of treating autoimmune and non-autoimmune diseases pathogenically related to the connective tissue which involves systemic delivery within a mammalian host of a therapeutic or prophylactic protein, RNA, ribozyme or any biologically active fragment thereof.

Systemic autoimmune diseases pathologically related to connective tissue amenable to treatment by the methods disclosed in the present invention include, but are not limited to, rheumatoid arthritis, systemic lupus erythematosus, Sjörgen's syndrome, polymyositis-dermatomyosis, systemic sclerosis (scleroderma), vasculitis syndromes, juvenile rheumatoid arthritis, ankylosing spondylitis, psoriatic arthritis and inflammatory bowel disease.

Additional non-immune diseases or disorders pathogenically related to connective tissue which are disclosed for treatment in the present invention include, but not limited to, osteoporosis, osteogenesis imperfecta, and Paget's disease.

3.2. NUCLEIC ACID SEQUENCES UTILIZED IN TREATING CONNECTIVE TISSUE DISEASES

The present invention discloses in vivo expression of a specific gene product or biologically active fragment thereof so as to provide therapeutic or prophylactic relief to an autoimmune or non-autoimmune disease pathogenically related to the connective tissue, thereby generating an acceptable level of resistance. The present invention is based in part on the strategy of local or systemic delivery of nucleic acid sequences which may provide a comprehensive approach to treating such diseases. In particular, these nucleic acid sequences should encode gene products which address one or more of the inflammatory, hypertrophic and erosive components of the disease. Nucleic acid sequences which combat one or more of these pathological components may be utilized in practicing the invention.

A nucleic acid sequence encoding a cytokine or a biologically active fragment thereof may be used to practice the present invention. Therapeutic or prophylactic cytokines of the present invention which reduce systemic inflammation include, but are in no way limited to, (1) the IL-1 receptor antagonist gene (IL-1ra or IRAP) or a biologically active fragment thereof; (2) IL-4 or a biologically active fragment thereof; and (3) IL-10 or a biologically active fragment thereof.

A nucleic acid sequence encoding an anticytokine or a biologically active fragment thereof may be used to practice the present invention. Therapeutic or prophylactic anticytokines, which will antagonize their cognate cytokine and in turn act in an anti-inflammatory manner include, but are in no way limited to (1) a soluble receptor of IL-1 or a biologically active fragment thereof; (2) a soluble receptor of TNF-α biologically active fragment thereof; and (3) a soluble receptor of IL-6 or a biologically active fragment thereof.

A nucleic acid sequence encoding an inhibitor of metalloproteinases or a biologically active fragment thereof may be used to practice the present invention. Therapeutic or prophylactic inhibitors of metalloproteinases inhibit cartilage breakdown, thus antagonizing the erosive properties of the diseases to be treated in the present invention. An enzyme inhibitor of metalloproteinases useful in the present invention includes, but is in no way limited to, TIMP.

A nucleic acid sequence encoding an antiadhesion molecule so as to inhibit cell-cell or cell-matrix interactions prominent in the early stages of an inflammatory response may be used to practice the present invention. Therapeutic or prophylactic inhibitors of cell-cell or cell-matrix interactions include, but are not limited to, soluble ICAM-1, soluble CD44, soluble CD18 or biologically active fragments of soluble ICAM-1, soluble CD44 or soluble CD18.

A nucleic acid sequence encoding an anti-oxidant, including but not necessarily limited to (1) superoxide dismutase, or a biologically active fragment thereof; and (2) an inhibitor of nitric oxide synthase, or biologically active fragment thereof, will provide comprehensive treatment regarding the degenerative effect of free radicals in the progression of the diseases to be treated in the present invention.

Other nucleic acid sequences encoding therapeutic or prophylactic gene products or biologically active fragments thereof may be used to practice the present invention. Such gene products may include cartilage growth factors, including but not limited to, (1) IGF-1 or a biologically active fragment thereof, and (2) TGF-β or a biologically active fragment thereof. Additionally, a nucleic acid encoding a constituent of the extracellular matrix, including but not limited to collagen, may express a gene product promoting therapeutic relief from one or more of the diseases targeted for treatment, as disclosed in the specification.

3.3. VIRAL AND NON-VIRAL MEDIATED DELIVERY SYSTEMS

The invention is also based on the use of various systems for gene transfer of the recombinant vector containing a nucleic acid sequence to be expressed within the mammalian host. The nucleic acid sequence of interest may be prepared for delivery by viral or non-viral mediated strategies.

Virus vectors utilized in the present invention include, but are not limited to (a) retroviral vectors, including but not limited to vectors derived from Moloney murine leukemia virus (MoMLV); (b) adenovirus vectors; (c) adeno-associated vectors; (d) herpes simplex virus vectors; (e) SV40 vectors; (f) polyoma virus vectors; (g) papilloma virus vectors; (h) picornavirus vectors; and (i) vaccinia virus vectors. Depending on the virus vector system chosen, techniques available to the skilled artisan are utilized to infect the target cell of choice with the recombinant virus vector.

A non-viral vector may be utilized in the present invention, such as, but not solely limited to, plasmid DNA. The use of plasmid DNA will be especially useful in non-viral vector mediated local delivery systems, such as direct injection of naked DNA into the skeletal muscle.

To this end, non-viral mediated delivery systems utilized in the present invention include, but are not limited to (a) direct injection of naked DNA; (b) liposome mediated transduction; (c) calcium phosphate [Ca$_3$(PO$_4$)$_2$] mediated cell transfection, the genetically transformed cells then returned extraarticularly to the mammalian host; (d) mammalian host cell transfection by electroporation, the genetically transformed cells then returned extraarticularly to the mammalian host; (e) DEAE-dextran mediated cell transfection, the genetically transformed cells then returned extraarticularly to the mammalian host; (f) polybrene mediated delivery; (g) protoplast fusion; (h) microinjection; and (i) polylysine mediated transduction.

3.4. SYSTEMIC DELIVERY OF THERAPEUTIC OR PROPHYLACTIC EXPRESSION PRODUCTS

The invention is based further on promoting systemic delivery of the therapeutic or prophylactic expression product of the nucleic acid sequence within the mammalian host. Preferred systemic delivery of the gene products entails use of a recombinant viral or non-viral vector followed by in vitro transfection of specific mammalian cell populations, recovery and purification of the transfected cells and administration to the patient. The specific cell populations utilized as targets for transfection by the recombinant vector containing a nucleic acid sequence of interest may include, but are not limited to, (1) bone marrow cell populations containing hematopoietic progenitor cells; (2) peripheral blood leukocyte populations, preferably CD34+ blood leukocyte populations, which are enriched for hematopoietic cells and can be utilized to repopulate the transfected hematopoietic cells upon introduction into the patient without ablation; (3) peripheral blood lymphocyte populations; (4) myoblast cells, which may be transplanted back into the host subsequent to in vitro transfection of the nucleic acid sequence of interest; and (5) delivery of the recombinant viral or non-viral vector containing the nucleic acid sequence of interest, or the nucleic acid sequence itself, by intramuscular injection into skeletal muscle.

Various combinations of the hereinbefore disclosed steps to treat a specific disease or disorder may be utilized. The malady to be treated may respond more favorably to in vivo expression of a specific systemically delivered gene or gene fragment, the gene or gene fragment being amenable to delivery via one or several modes of vector construction and cellular delivery such that the gene is expressed and the prophylactic or therapeutic protein or protein fragment is systemically delivered throughout the mammalian host. Upon review of this disclosure, it will be within the purview of the skilled artisan to pick and choose between the therapeutic genes and modes of delivery disclosed in the present invention so as to select an efficient method of treatment. Various combinations and preferred embodiments are disclosed and expanded upon.

3.5. TREATMENT OF RHEUMATOID ARTHRITIS

In one embodiment of the invention, a DNA sequence encoding IRAP or a biologically active portion thereof is administered to a patient so as to promote systemic and prolonged distribution of the expressed IRAP gene product for treatment, either therapeutic or prophylactic in nature, of rheumatoid arthritis.

In a further embodiment of the invention relating to the treatment of rheumatoid arthritis, any of the viral vectors, non-viral vectors or methods of delivering the nucleic acid sequence of interest to the target cell may be utilized to provide systemic application of the gene product or biologically active fragment thereof.

In a specific embodiment regarding the IRAP induced treatment of rheumatoid arthritis, the DNA sequence encoding IRAP or a portion thereof is subcloned into a retroviral vector prior to administration to the patient.

Regarding use of a retroviral vector in IRAP induced treatment of rheumatoid arthritis, the retroviral vector may be a MoMLV retroviral vector, resulting in an MoMLV-IRAP construction.

In a specific embodiment regarding the recombinant MoMLV-IRAP construction in the treatment of rheumatoid arthritis, the recombinant MoMLV-IRAP construction is MFG-IRAP (FIG. 1 and FIG. 2 [SEQ ID NO:3] for IRAP cDNA clone utilized in construction of MFG-IRAP).

In regards to promoting systemic delivery of the MFG-IRAP construction in the treatment of rheumatoid arthritis, this retroviral vector is transferred into a standard retroviral packaging cell line, the recovered viral particles used to transfect a mammalian cell population line, including but not limited to (1) bone marrow cell populations containing hematopoietic progenitor cells; (2) peripheral blood leukocyte populations, preferably CD34+ blood leukocyte populations, which are enriched for hematopoietic cells; (3) peripheral blood lymphocyte populations; and (4) myoblast cells, which may be transplanted back into the host subsequent to in vitro transfection. The in vitro transfected cell populations of (1), (2) and (3) are then reintroduced intravenously into the circulatory system of the patient.

In a preferred embodiment of the invention regarding the systemic delivery of the MFG-IRAP construction in the treatment of rheumatoid arthritis, this retroviral vector is transferred into a standard retroviral packaging cell line, the recovered viral particles used to transfect bone marrow cell populations containing hematopoietic progenitor cells and these in vitro transfected cell populations are then reintroduced intravenously into the circulatory system of the patient.

In an additional embodiment regarding treatment of rheumatoid arthritis, a viral or non-viral recombinant vector molecule may be transferred directly into the skeletal muscle by intramuscular injection. In a preferred mode of this technique, the recombinant vector molecule is a plasmid, the IRAP gene or gene fragment thereof being subcloned downstream of a regulatory sequence(s) such that continual promotion of expression of the IRAP gene or gene fragment thereof will occur subsequent to intramuscular injection.

In a further embodiment regarding treatment of rheumatoid arthritis, any of the strategies disclosed within the specification may be utilized for targeting a nucleic acid of interest to the appropriate cell type so as to promote expression of the therapeutic agent, including but not necessarily limited to a nucleic acid sequence encoding (1) a soluble receptor of IL-1 or a biologically active fragment thereof; (2) IL-4 or a biologically active fragment thereof; (3) IL-10 or a biologically active fragment thereof; (4) a soluble receptor of TNF-α or a biologically active fragment thereof; (5) a nucleic acid sequence encoding an inhibitor of metalloproteinases or a biologically active fragment thereof, such as TIMP; (6) a nucleic acid sequence encoding an antiadhesion molecule such as soluble ICAM-1, soluble CD44, soluble CD18 or biologically active fragments of soluble ICAM-1, soluble CD44 or soluble CD18; (7) a nucleic acid sequence encoding an anti-oxidant, such as superoxide dismutase, or a biologically active fragment thereof, and an inhibitor of nitric oxide synthase, or biologically active fragments thereof; (8) a nucleic acid sequence encoding IGF-1 or a biologically active fragment thereof, and TGF-β or a biologically active fragment thereof; and (9) a nucleic acid fragment encoding constituents of the extracellular matrix, such as collagen.

3.6. TREATMENT OF SYSTEMIC LUPUS ERYTHEMATOSUS

In another embodiment of the invention, a DNA sequence encoding IRAP or a biologically active portion thereof is administered to a patient so as to promote systemic and prolonged distribution of the expressed IRAP gene product for treatment, either therapeutic or prophylactic in nature, of systemic lupus erythematosus.

In a further embodiment of the invention relating to the treatment of systemic lupus erythematosus, any of the viral vectors, non-viral vectors or methods of delivering the nucleic acid sequence of interest to the target cell may be utilized to provide systemic application of the therapeutic gene product of biologically active fragment thereof.

In a specific embodiment regarding the IRAP induced treatment of systemic lupus erythematosus, the DNA sequence encoding IRAP or a portion thereof is subcloned into a retroviral vector prior to administration to the patient.

Regarding use of a retroviral vector in IRAP induced treatment of systemic lupus erythematosus, the retroviral vector may be a MoMLV retroviral vector, resulting in an MoMLV-IRAP construction.

In a specific embodiment regarding the recombinant MoMLV-IRAP construction in the treatment of systemic lupus erythematosus, the recombinant MoMLV-IRAP construction is MFG-IRAP (FIG. 1).

In regards to promoting systemic delivery of the MFG-IRAP construction in the treatment of systemic lupus erythematosus, this retroviral vector is transferred into a standard retroviral packaging cell line, the recovered viral particles used to transfect a mammalian cell population line, including but not limited to (1) bone marrow cell populations containing hematopoietic progenitor cells; (2) peripheral blood leukocyte populations, preferably CD34+blood leukocyte populations, which are enriched for hematopoietic cells; (3) peripheral blood lymphocyte populations; and (4) myoblast cells, which may be transplanted back into the host subsequent to in vitro transfection. The in vitro transfected cell populations of (1) and (3) are then reintroduced intravenously into the circulatory system of the patient.

In a preferred embodiment of the invention regarding the systemic delivery of the MFG-IRAP construction in the treatment of systemic lupus erythematosus, this retroviral vector is transferred into a standard retroviral packaging cell line, the recovered viral particles are used to transfect bone marrow cell populations containing hematopoietic progenitor cells and these in vitro transfected cell populations are then reintroduced into the circulatory system of the patient.

In an additional embodiment regarding treatment of systemic lupus erythematosus, a viral or non-viral recombinant vector molecule may be transferred locally into the skeletal muscle by direct intramuscular injection. In a preferred mode of this technique, the recombinant vector molecule is a plasmid, the IRAP gene or gene fragment thereof being subcloned downstream of a regulatory sequence(s) such that continued expression of the IRAP gene or gene fragment thereof will occur within the transfected tissue.

In a further embodiment regarding treatment of systemic lupus erythematosus, any of the strategies disclosed within the specification may be utilized for targeting a nucleic acid of interest to the appropriate cell type so as to promote expression of the therapeutic agent, including but not necessarily limited to a nucleic acid sequence encoding (1) a soluble receptor of IL-1 or a biologically active fragment thereof; (2) interleukin-4 or a biologically active fragment thereof; (3) interleukin-10 or a biologically active fragment thereof; (4) a soluble receptor of TNF-α or a biologically active fragment thereof; (5) a nucleic acid sequence encoding an inhibitor of metalloproteinases or a biologically active fragment thereof, such as TIMP; (6) a nucleic acid sequence encoding an antiadhesion molecule such as soluble ICAM-1, soluble CD44, soluble CD18 or biologically active fragments of soluble ICAM-1, soluble CD44 or soluble CD18; (7) a nucleic acid sequence encoding an anti-oxidant, such as superoxide dismutase, or a biologically active fragment thereof, and an inhibitor of nitric oxide synthase, or biologically active fragments thereof; (8) a nucleic acid sequence encoding IGF-1 or a biologically active fragment thereof, and TGF-β or a biologically active fragment thereof; and (9) a nucleic acid fragment encoding constituents of the extracellular matrix, such as collagen.

3.7. TREATMENT OF ADDITIONAL CONNECTIVE TISSUE DISEASES

In additional embodiments of the invention, treatment of other autoimmune disease which affect connective tissue, including but not limited to Sjörgen's syndrome, polymyositis-dermatomyositis, systemic sclerosis (scleroderma), vasculitis syndromes, juvenile rheumatoid arthritis, ankylosing spondylitis, psoriatic arthritis and inflammatory bowel disease. Additional non-immune diseases or disorders pathogenically related to the connective tissue which are disclosed for treatment in the present invention include, but not limited to, osteoporosis, osteogenesis imperfecta, and Paget's disease. Treatment of these diseases involves the prolonged, systemic delivery of therapeutic or prophylactic expression products encoded by nucleic acid sequences which include but are not solely limited to (1) IRAP or a biologically active fragment thereof; (2) a soluble receptor of IL-1 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1 and soluble CD-44, or biologically active fragments of soluble ICAM-1 or soluble CD-44; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid sequence encoding IGF-1 or a biologically active fragment thereof, and TGF-β or a biologically active fragment thereof; (10) a nucleic acid fragment encoding constituents of the extracellular matrix, such as collagen; and (11) a soluble receptor of IL-6 or a biologically active fragment thereof. Any of the strategies disclosed within the specification may be utilized for the systemic delivery of these DNA sequences to a mammalian host in treating the hereinbefore mentioned diseases.

It is an object of the invention to provide prolonged relief against autoimmune and non-autoimmune diseases affecting connective tissue by systemic delivery of a therapeutic or prophylactic amount of a protein, protein fragment, antisense RNA or ribozyme within a mammalian host; these gene products encoded by a nucleic acid sequence delivered to the mammalian host in a local or systemic manner.

It is another object of the invention to locally or systemically deliver the IRAP gene or gene fragment capable of prolonged expression to a mammalian host so as to provide systemic relief against various autoimmune and non-autoimmune diseases that elicit pathological degradation of connective tissue.

It is a further object of the invention to locally or systemically deliver the IRAP gene or a biologically active gene fragment capable of prolonged expression to a mammalian host so as to provide systemic relief against rheumatoid arthritis or systemic lupus erythematosus.

It is a specific object of the invention to locally or systemically deliver the IRAP gene or a biologically active gene fragment to a mammalian host by transfecting hematopoietic cell containing populations so as to systemically repopulate the mammalian host with the IRAP-transfected hematopoietic cells; allowing for treatment of autoimmune diseases affecting connective tissue including but not limited to rheumatoid arthritis or systemic lupus erythematosus as well as hereinbefore disclosed non-autoimmune diseases affecting connective tissue.

These and other objects of the invention will be more fully understood from the following description of the invention in context of additional gene treatment of autoimmune and non-autoimmune diseases affecting connective tissue, the referenced figure attached hereto and the claims appended hereto.

3.8. DEFINITIONS The terms listed below, as used herein, will have the meanings indicated.

| | |
|---|---|
| IRAP | Interleukin-1 Receptor Antagonist Protein |
| IL-1ra | Interleukin-1 Receptor Antagonist Protein |
| RNA | Ribonucleic Acid |
| DNA | Deoxyribonucleic acid |
| LTR | Long Terminal Repeats |
| IL-1 | Interleukin-1 |
| IL-2 | Interleukin-2 |
| IL-3 | Interleukin-3 |
| IL-4 | Interleukin-4 |
| IL-6 | Interleukin-6 |
| IL-10 | Interleukin-10 |
| TNF-α | Tumor Necrosis Factor - alpha |
| MoMLV | Moloney Murine Leukemia Virus |
| PDGF | Platelet Derived Growth Factor |
| SSc | Systemic Sclerosis |
| SLE | Systemic Lupus Erythematosus |
| RA | Rheumatoid Arthritis |
| NSAID | Nonsteroidal Anti-inflammatory Drug |
| TIMP | Tissue Inhibitor of Metalloproteinase |
| TGB-β | Type β Transforming Growth Factor |

As used herein, the term "patient" includes members of the animal kingdom including but not limited to human beings.

As used herein, the term "mammalian host" includes members of the animal kingdom including but not limited to human beings.

As used herein, the term "treatment" includes promotion of either therapeutic relief or prophylactic resistance, depending upon the specific connective tissue disease or disorder to be treated, from proteins, peptides or chemical compounds which induce inflammatory or erosive responses during pathogenesis of said connective tissue disease or disorder.

As used herein, the term "biologically active fragment" refers to any portion or derivative of the corresponding wild-type molecule exhibiting biological activity by promoting therapeutic relief or prophylactic resistance from proteins, peptides or chemical compounds which induce inflammatory or erosive responses during pathogenesis of a connective tissue disease or disorder.

4. BRIEF DESCRIPTION OF THE FIGURES

FIG. 1 shows a schematic representation of the provirus form of Moloney murine leukemia virus (MoMLV) that is used for the construction of retroviral vectors. The MFG retroviral vector is a simplified MoMVL retroviral vector in which the DNA sequences encoding the pol and env proteins have been deleted. A cDNA encoding human IRAP (FIG. 2) was inserted into the NcoI and BamHI cloning sites of the retroviral vector MFG. Specifically, a Pst1 to BamHI fragment from the IRAP cDNA was linked to a synthetic oligonucleotide adapter from the NcoI site (representing the start site of translation for IRAP) to the Pst1 site (approximately 12 base pairs downstream from the NcoI site) to the MFG backbone digested at NcoI and BamHI in a three part ligation reaction. The straight arrow and the crooked arrow represent unspliced and spliced messenger RNAs respectively. IRAP is encoded by the spliced message. The BAG vector is an MFG derivative. In BAG, the, β-gal gene is expressed from a non-spliced LTR-driven message whereas the neo gene is expressed from a SV40 promoter. Both MFG-IRAP and BAG have the psi site required for packaging of the recombinant RNA into virions.

FIG. 2 shows the cloned IRAP cDNA sequence (SEQ ID NOS:3 and 4) utilized in construction of MFG-IRAP.

namely a HindIII fragment comprising the entire coding region of human IRAP, as described in detail in Example Section 6.1.1; SEQ ID NO 3 is the nucleotide sequence and SEQ ID 4 is the amino acid sequence for human IRAP.

5. DETAILED DESCRIPTION OF THE INVENTION

The present invention relates to methods of gene treatment involving local or systemic delivery within a mammalian host of a nucleic acid sequence which expresses a therapeutic or prophylactic protein or protein fragment, antisense RNA, ribozyme or other biologically active fragment. Construction and utilization of a viral or non-viral recombinant vector and the ability of the locally or systemically delivered nucleic acid sequence within the recombinant vector for sustained expression within the mammalian host is tantamount to a perpetual systemic drug delivery system. The methods of the present invention disclose connective tissue diseases or disorders targeted for therapeutic or prophylactic treatment. DNA sequences available for delivery to the mammalian host, strategies to prepare and deliver the DNA sequence so as to optimize expression and availability of the biologically active product, as well as preferred combinations of these strategies in treating these systemic connective tissue disorders. The present invention also discloses recombinant viral and non-viral vectors for utilization in treating the connective tissue disorders discussed throughout the specification.

5.1. NUCLEIC ACID SEQUENCES UTILIZED IN TREATING CONNECTIVE TISSUE DISEASES

The present invention discloses in vivo expression of a specific gene product or biologically active fragment thereof so as to provide therapeutic or prophylactic relief to an autoimmune or non-autoimmune disease pathogenically related to a connective tissue, thereby generating an acceptable level of resistance. The present invention is based in part on the strategy of local or systemic delivery of a nucleic acid sequence which may provide a comprehensive approach to treating such diseases. In particular, these nucleic acid sequences should encode gene products which address one or more of the inflammatory, hypertrophic and erosive components of the disease. A nucleic acid sequence which combats one or more of these pathological components may be utilized in practicing the invention. It will become evident upon review of this specification that more than one nucleic acid sequence may be simultaneously administered to the patient to promote systemic treatment of the respective connective tissue disease.

A nucleic acid sequence encoding a cytokine or a biologically active fragment thereof may be used to practice the present invention. Therapeutic or prophylactic cytokines of the present invention which reduce systemic inflammation include, but are in no way limited to, (1) the IL-1 receptor antagonist gene (IL-1ra or IRAP) or a biologically active fragment thereof; (2) IL-4 or a biologically active fragment thereof; and (3) IL-10 or a biologically active fragment thereof.

A nucleic acid sequence encoding an anticytokine or a biologically active fragment thereof may be used to practice the present invention. Therapeutic or prophylactic anticytokines, which will antagonize their cognate cytokine and in turn act in an anti-inflammatory manner include, but are in no way limited to (1) a soluble receptor of IL-1 or a biologically active fragment thereof; and (2) a soluble receptor of TNF-α or a biologically active fragment thereof.

A nucleic acid sequence encoding an inhibitor of metalloproteinases or a biologically active fragment thereof may be used to practice the present invention. Therapeutic or prophylactic inhibitors of metalloproteinases inhibit cartilage breakdown, thus antagonizing the erosive properties of the diseases to be treated in the present invention. An enzyme inhibitor of metalloproteinases useful in the present invention includes, but is in no way limited to, TIMP.

A nucleic acid sequence encoding an antiadhesion molecule so as to inhibit cell-cell or cell-matrix interactions prominent in the early stages of an inflammatory response may be used to practice the present invention. Therapeutic or prophylactic inhibitors of cell-cell or cell-matrix interactions includes, but is in not limited to, soluble ICAM-1, soluble CD44, soluble CD18 or biologically active fragments of soluble ICAM-1, soluble CD44 or soluble CD18.

A nucleic acid sequence encoding an anti-oxidant, including but not necessarily limited to (1) superoxide dismutase, or a biologically active fragment thereof; and (2) an inhibitor of nitric oxide synthase, or biologically active fragments thereof, will provide comprehensive treatment regarding the degradative effect of free radicals in the progression of the diseases to be treated in the present invention.

Other nucleic acid sequences encoding therapeutic or prophylactic gene products or biologically active fragments thereof may be used to practice the present invention. Such gene products may include cartilage growth factors, including but not limited to, (1) IGF-1 or a biologically active fragment thereof, and (2) TGF-β or a biologically active fragment thereof. Additionally, constituents of the extracellular matrix, including but not limited to collagen, may provide therapeutic relief from one or more of the diseases targeted for treatment, as disclosed in the specification.

5.2. VIRAL AND NON-VIRAL MEDIATED DELIVERY SYSTEMS

The invention is also based on the use of various systems for gene transfer of the recombinant vector containing a nucleic acid sequence to be expressed within the mammalian host. The nucleic acid sequence of interest may be prepared for delivery by viral or non-viral mediated strategies.

Virus vectors utilized in the present invention include, but are not limited to (a) retroviral vectors, including but not limited to vectors derived from Moloney murine leukemia virus (MoMLV); (b) adenovirus vectors; (c) adeno-associated vectors; (d) herpes simplex virus vectors; (e) SV40 vectors; (f) polyoma virus vectors; (g) papilloma virus vectors; (h) picornavirus vectors; and (i) vaccinia virus vectors. Depending of the virus vector system chosen, techniques available to the skilled artisan are utilized to infect the target cell of choice with the recombinant virus vector.

In a specific embodiment of the invention, a Moloney murine leukemia virus (MoMLV) retroviral vector is utilized to generate a construct for transfection of mammalian cells. Although MoMLV is a RNA virus, it has a DNA intermediate form that stably integrates into the genome of the host cell. The virus has two long terminal repeats (LTRs) at the 5' and 3' ends of proviral DNA that contain promoter, polyadenylation, and integration sequences required for the viral life cycle. A packaging sequence, termed psi, is also required in cis or the production of infectious virus. The virus encodes three proteins, gag, pol, and env, that are required in trans for viral replication. The gag and pol proteins are expressed from a non-spliced message whereas the env protein is expressed from a spliced message generated using the 5' and 3' splice sites shown in FIG. 1. To generate a recombinant retroviral vector, the gag, pol, and env genes were removed and the cDNA encoding IRAP (MFG-IRAP) or the genes for β-gal and neo (BAG) were inserted. In MFG-IRAP, the gene is expressed from a LTR-driven spliced message. In BAG, the, β-gal gene is expressed from a non-spliced LTR-driven message whereas the neo gene is expressed from a SV40 promoter. Both MFG-IRAP and BAG have the psi site required for packaging of the recombinant RNA into virions. To generate infectious virus, the proviral DNA is transfected into a packaging line that constitutively produces gag, pol, and env proteins. FIG. 1 shows the structure of the cDNA encoding the human interleukin-1 receptor antagonist protein (IRAP) gene inserted into the NcoI and BamHI cloning sites of the retroviral vector MFG (for a review of retroviral vectors, see Miller, 1992, Current Topics in Microbiology and Immunology 158: 1–24).

Any non-viral vector may be utilized in the present invention, such as, but not solely limited to, plasmid DNA. The use of plasmid DNA will be especially useful in non-viral vector mediated systemic delivery systems, such as direct injection of naked DNA into skeletal muscle. Any eukaryotic promoter and/or enhancer sequence available to the skilled artisan which is known to up-regulate expression of the nucleic acid of interest may be used in plasmid vector constructions, including but not limited to a cytomegalovirus (CMV) promoter, a Rous Sarcoma virus (RSV) promoter, a Murine Leukemia Virus (MLV) promoter, a β-actin promoter, as well as any cell-specific eukaryotic promoter sequence that would be known to be active in the cell targeted for transduction. To this end, non-viral mediated delivery systems utilized in the present invention include, but are not limited to (a) direct injection of naked DNA; (b) liposome mediated transduction; (c) calcium phosphate [Ca$_3$(PO$_4$)$_2$] mediated cell transfection, the genetically transformed cells then returned extraarticularly to the mammalian host; (d) mammalian host cell transfection by electroporation, the genetically transformed cells then returned extraarticularly to the mammalian host; (e) DEAE-dextran mediated cell transfection, the genetically transformed cells then returned extraarticularly to the mammalian host; (f) polybrene mediated delivery; (g) protoplast fusion; (h) microinjection; and (i) polylysine mediated transformation.

5.3. SYSTEMIC DELIVERY OF THERAPEUTIC OR PROPHYLACTIC EXPRESSION PRODUCTS

The invention is based further on promoting systemic delivery of the therapeutic or prophylactic expression product of the nucleic acid sequence within the mammalian host. Preferred systemic delivery of the gene products entails use of a recombinant viral or non-viral vector followed by in vitro transfection of specific mammalian cell populations, recovery and purification of the transfected cells and administration to the patient. The specific cell populations utilized as targets for transfection by the recombinant vector containing a nucleic acid sequence of interest may include, but are not limited to, (1) bone marrow cell populations containing hematopoietic progenitor cells; (2) peripheral blood leukocyte populations, preferably CD34+ blood leukocyte populations, which are enriched for hematopoietic cells and can be utilized to repopulate the transfected hematopoietic cells upon introduction into the patient without ablation; (3) peripheral blood lymphocyte populations; (4) myoblast cells, which may be transplanted back into the host subsequent to in vitro transfection of the nucleic sequence of interest; and (5) delivery of the recombinant viral or non-viral vector containing the nucleic acid sequence of interest, or the nucleic acid sequence itself, by intramuscular injection.

The use of bone marrow containing hematopoietic progenitor cells is described in detail in Example Section 6. Briefly, bone marrow cells are removed, infected with the recombinant virus, and reintroduced back into the mammalian host. Thus, a gene or gene fragment is systemically distributed within the mammalian host, expression of this DNA sequence resulting in systemic delivery of the gene product within the mammalian host.

Peripheral blood is a source of mammalian cells for infection by viral mediated vectors. More specifically, blood leukocytes, especially the CD34+ population which contain the circulating hematopoietic stem cells, may be used as target cells for viral infection, followed by repopulation of the mammalian host marrow without ablation (Karlsson, et al., 1993, Bone Marrow Transplant. 11(supp. 1): 124–127). Additionally, lymphocytes may also be utilized as target cells to promote systemic delivery of the nucleic acid sequence of interest. The lymphocytes may be removed from the peripheral blood of the host, cultured by known techniques and used as the target cell population for infection by viral vectors containing the nucleic acid sequence of interest. The infected lymphocytes may then be injected into the mammalian host (e.g., see Anderson, et al., 1990, Human Gene Therapy 1: 331–361).

An additional target cell population are myoblasts. Blood flow into the relatively large mass of skeletal muscle renders this tissue a localized repository for the nucleic acid sequence of interest. Therefore, in vitro infection and reintroduction of myoblast cells into the mammalian host provides a local target within the host which results in systemic delivery of the therapeutic product. Myoblast culture, infection and reintroduction into the host can be achieved by known techniques (e.g., see Dai, et al., 1992, Proc. Natl. Acad. Sci. USA 89: 10892–10895).

To this end, direct injection into skeletal muscle is an additional method for local delivery of the vector molecule. Direct injection ultimately results, upon expression of the gene product, in systemic delivery of the therapeutic product within the mammalian host (Wolff, et al, 1990, Science 247: 1465–1468; Raz, et al., 1993, Proc. Natl. Acad. Sci. USA 90:4523–4527). Direct injection of naked DNA, preferably a non-viral vector such as plasmid DNA, is utilized in this mode of localized delivery. Any eukaryotic promoter and/or enhancer sequence available to the skilled artisan which is known to up-regulate expression of the nucleic acid of interest may be used in plasmid vector constructions, including but not limited to a cytomegalovirus (CMV) promoter, a Rous Sarcoma virus (RSV) promoter, a Murine Leukemia Virus (MLV) promoter, a β-actin promoter, as well as any cell-specific eukaryotic promoter sequence that would be known to be active in the cell targeted for transduction.

5.4. TREATMENT OF CONNECTIVE TISSUE DISEASES

5.4.1. SYSTEMIC TREATMENT OF RHEUMATOID ARTHRITIS

Rheumatoid arthritis is a multisystem, chronic disease widely held to be an autoimmune disease. Approximately 80% of patients are positive for an autoantibody referred to as rheumatoid factor (RF). Rheumatoid factor is raised against the Fc portion of autologous IgG. Additional autoantibodies to nuclear elements, collagen and cytoskeletal filamentous proteins may also be detected. Rheumatoid arthritis most often results in a severe form of chronic synovitis. In addition to this chronic inflammation of the synovial tissue, cell-mediated immunity is also activated, resulting in cartilaginous destruction. It is not known what triggers the autoimmune reaction, but IL-1 may well be a major mediator of rheumatoid arthritis. First, IL-1 is known to activate synovial cells and promote cartilaginous breakdown. Second, IL-1 acts as a chemoattractant for lymphocytes and macrophages, which are thought to play a major role in the pathogenesis of rheumatoid arthritis.

The present invention discloses and teaches a first line systemic defense encompassing utilization of a DNA sequence encoding a protein or protein fragment which antagonizes IL-1 (e.g., IRAP or a soluble receptor to IL-1), downregulates IL-1(IL-4 and IL-10) or acts to induce IRAP in vivo (IL-4 and IL-10). Additionally nucleic acid sequences which may be utilized to combat inflammation and cartilage destruction include (1) a soluble receptor of TNF-α or a biologically active fragment thereof; (2) a nucleic acid sequence encoding an inhibitor of metalloproteinases or a biologically active fragment thereof, such as TIMP; (3) a nucleic acid sequence encoding an antiadhesion molecule such as soluble ICAM-1, soluble CD44, soluble CD18 or biologically active fragments of soluble ICAM-1, soluble CD44 or soluble CD18; (4) a nucleic acid sequence encoding an anti-oxidant, such as superoxide dismutase, or a biologically active fragment thereof, and an inhibitor of nitric oxide synthase, or biologically active fragments thereof; (5) a nucleic acid sequence encoding IGF-1 or a biologically active fragment thereof, and TGF-β or a biologically active fragment thereof; and (6) a nucleic acid fragment encoding constituents of the extracellular matrix, such as collagen. Administration and delivery of these respective nucleic acid sequences may be directed by viral or non-viral mediated methods as disclosed throughout the specification.

One embodiment of the invention teaches the delivery of a DNA sequence encoding IRAP or a biologically active protein fragment thereof. The delivery and continuous expression of the DNA sequence of interest promotes prolonged distribution of the expressed IRAP protein or protein fragment for therapeutic relief from rheumatoid arthritis.

In a further embodiment regarding the IRAP induced systemic treatment of rheumatoid arthritis, the DNA sequence encoding IRAP or a portion thereof is subcloned into a MoMLV retroviral vector prior to systemic delivery to the patient. Specifically, a recombinant MoMLV-IRAP construction that may be utilized in the treatment of rheumatoid arthritis is MFG-IRAP (FIG. 1), wherein the DNA sequence encoding IRAP or a portion thereof is SEQ ID NO:3 (FIG. 2).

In regards to promoting systemic delivery of the MFG-IRAP construction in the treatment of rheumatoid arthritis, this retroviral vector is transferred into a standard retroviral packaging cell line, the recovered viral particles used to transfect a mammalian cell population line, including but not limited to (1) bone marrow cell populations containing hematopoietic progenitor cells; (2) peripheral blood leukocyte populations, preferably CD34+ blood leukocyte populations, which are enriched for hematopoietic cells; (3) peripheral blood lymphocyte populations, which are then reintroduced intravenously into the circulatory system of the patient; and (4) myoblast cells, which may be transplanted back into the host subsequent to in vitro transfection of the nucleic acid sequence of interest.

In a preferred embodiment of the invention regarding systemic delivery of the MFG-IRAP construction for treatment of rheumatoid arthritis, this retroviral vector is transferred into a standard retroviral packaging cell line and the recovered viral particles are used to transfect bone marrow cell populations containing hematopoietic progenitor cells. These in vitro transfected cell populations are then reintroduced into the circulatory system of the patient as described in Example Section 6.

5.4.2. SYSTEMIC TREATMENT OF SYSTEMIC LUPUS ERYTHEMATOSUS

Systemic lupus erythematosus (SLE) is an autoimmune disease characterized by injury to the skin, joints, kidney and serosal membrane. A vast array of autoantibodies, especially antinuclear antibodies, are present in the SLE patient. Pathogenesis of SLE includes damage to tissues and cells from deposition of autoantibodies and immune complexes. A major immunologic factor in the pathogenesis of SLE is thought to be B-cell hyperactivity. While no cure currently exists, treatment of SLE has been directed at controlling inflammation, usually by administration of salicylates, NSAIDs or steroids.

The present invention discloses, in part, the ability to control or substantially reduce SLE induced inflammation and tissue damage by systemic or local delivery, prolonged exposure, and expression within the patient of DNA sequences encoding an IL-1 antagonist. As discussed hereinbefore in regards to treating rheumatoid arthritis, examples of such IL-1 antagonists include, but are not limited to, DNA sequence encoding IRAP, soluble receptor of IL-1, IL-4, IL-10 or biologically active protein fragments thereof.

As disclosed for treatment of rheumatoid arthritis, additional nucleic acid sequences which may be utilized to combat inflammation and cartilage destruction caused by SLE include, but are not solely limited to (1) a soluble receptor of TNF-β or a biologically active fragment thereof; (2) a nucleic acid sequence encoding an inhibitor of metalloproteinases or a biologically active fragment thereof, such as TIMP; (3) a nucleic acid sequence encoding an antiadhesion molecule such as soluble ICAM-1, soluble CD44, soluble CD18 or biologically active fragments of soluble ICAM-1, soluble CD44 or soluble CD18; (4) a nucleic acid sequence encoding an anti-oxidant, such as superoxide dismutase, or a biologically active fragment thereof, and an inhibitor of nitric oxide synthase, or biologically active fragments thereof; (5) a nucleic acid sequence encoding IGF-1 or a biologically active fragment thereof, and TGF-β or a biologically active fragment thereof; and (6) a nucleic acid fragment encoding constituents of the extracellular matrix, such as collagen. Delivery and application of these respective nucleic acid sequences may be directed by viral or non-viral mediated methods as disclosed throughout the specification.

One embodiment of the invention teaches the delivery of a DNA sequence encoding IRAP or a biologically active protein fragment thereof. The delivery and continuous expression of the DNA sequence of interest promotes prolonged distribution of the expressed IRAP protein or protein fragment for therapeutic relief from SLE.

In a further embodiment regarding the IRAP induced systemic treatment of rheumatoid arthritis, the DNA sequence encoding IRAP or a portion thereof is subcloned into a MoMLV retroviral vector prior to systemic delivery to the patient. Specifically, a recombinant MoMLV-IRAP construction that may be utilized in the treatment of MFG-IRAP (FIG. 1), wherein the DNA sequence encoding IRAP or a portion thereof is SES ID NO:3 (FIG. 2).

In regards to promoting systemic delivery of the MFG-IRAP construction in the treatment of SLE, this retroviral vector is transferred into a standard retroviral packaging cell line, the recovered viral particles used to transfect a cell population include but are not limited to (1) bone marrow cell populations containing hematopoietic progenitor cells; (2) peripheral blood leukocyte populations, preferably CD34+ blood leukocyte populations, which are enriched for hematopoietic cells, which are then reintroduced intravenously into the circulatory system of the patient; and (4) myoblast cells, which may be transplanted back into the host subsequent to in vitro transfection of the nucleic acid sequence of interest.

In a preferred embodiment of the invention regarding the systemic delivery, of the MFG-IRAP construction in the treatment of SLE, this retroviral vector is transferred into a standard retroviral packaging cell line, the recovered viral particles used to transfect bone marrow cell populations containing hematopoietic progenitor cells, these in vitro transfected cell populations are then introduced into the bone marrow of the patient.

5.4.3. TREATMENT OF SYSTEMIC SCLEROSIS

Systemic sclerosis (SSc) is an inflammatory based disease characterized by multisystem disorders. The primary pathogenic event is endothelial cell injury followed by eventual proliferation, excessive fibrosis, and vessel obliteration. The cause of SSc is unknown. However, the disease is associated with a variety of immunologic events. Fibroblast activation, a cause of eventual fibrosis, is thought to involve stimulation by IL-1, TNF-α, TGF-β, PDGF, fibroblast growth factor, and other cytokines.

In regard to treatment of systemic sclerosis, any of the strategies disclosed within the specification may be utilized for a targeting nucleic acid of interest to the appropriate cell type so as to promote expression of the therapeutic agent, including but not necessarily limited to a nucleic acid sequence encoding (1) IRAP or a biologically active fragment thereof; (2) a soluble receptor of IL-1 or a biologically active fragment thereof; (3) IL-4 or a biologically active fragment thereof; (4) IL-10 or a biologically active fragment thereof; (5) the soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; and (8) a nucleic acid sequence encoding an antioxidant, such as superoxide dismutase, or a biologically active fragment thereof, and an inhibitor of nitric oxide synthase, or biologically active fragments thereof.

5.4.4. SYSTEMIC TREATMENT OF POLYMYOSOTIS-DERMATOMYOSITIS

Polymyositis is a chronic inflammatory myopathy initially characterized by muscle weakness and eventually resulting in motor disability. The disease is associated with dermatomyositis in approximately 50% of cases. The cause of the disease is unknown, but patients tend to accumulate autoantibodies to tRNA synthases. It has also been documented that cell-mediated immune injury via activation of CD4+ and CD8+ T-lymphocytes is involved in progression of the disorder.

Interleukin-1 is involved in T-cell activation. Therefore, another embodiment of the invention involves methods of treating polymyositis-dermatomyositis both locally and systemically. DNA sequences expressing antagonists of IL-1, as hereinbefore described, are delivered to sites of myopathy either systemically (e.g., via in vitro transfection of bone marrow or CD34+ cell populations followed by administration of the transfected cells to the patient) or locally (intramuscular injection or in vitro transfection and reintroduction of host myoblast cell populations).

In regard to treatment of polymyositis-dermatomyositis, any of the strategies disclosed within the specification may be utilized for targeting nucleic acid of interest to the appropriate cell type so as to promote expression of the therapeutic agent, including but not necessarily limited to a nucleic acid sequence encoding (1) IRAP or a biologically active fragment thereof; (2) a soluble receptor of IL-1 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid sequence encoding IGF-1 or a biologically active fragment thereof, and TGF-β or a biologically active fragment thereof; and (10) a nucleic acid sequence encoding constituents of the extracellular matrix, such as collagen.

5.4.5. SYSTEMIC TREATMENT OF SJÖGREN'S SYNDROME

Sjögren's syndrome is identified clinically by dry eyes and mouth resulting from a lymphocytic infiltration and destruction of the lacrimal and salivary glands. While a number of autoantibodies have been detected during pathogenesis of Sjögren's syndrome, the most prevalent are autoantibodies against ribonucleoprotein antigens. Most of the infiltrating immune cells are CD4+ T-cells, which are stimulated by IL-1.

Therefore, an additional embodiment of the invention relates to treatment of Sjögren's syndrome by generation and delivery of DNA sequences encoding an IL-1 antagonist, as disclosed and taught hereinbefore.

Preferred modes of systemic delivery in treating Sjögren's syndrome would be reintroduction of transduced bone marrow cells, leukocytes or lymphocytes. The preferable mode of local delivery would be intramuscular injection.

In a further embodiment regarding treatment of Sjögren's syndrome, any of the strategies disclosed within the specification may be utilized for targeting nucleic acid of interest to the appropriate cell type so as to promote expression of the therapeutic agent, including but not necessarily limited to a nucleic acid sequence encoding (1) IRAP or a biologically active fragment thereof; (2) a soluble receptor of IL-1 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid sequence encoding IGF-1 or a biologically active fragment thereof, and TGF-β or a biologically active fragment thereof; and (10) a nucleic acid fragment encoding constituents of the extracellular matrix, such as collagen.

5.4.6. SYSTEMIC TREATMENT OF VASCULITIS SYNDROMES

Vasculitis syndromes are characterized by inflammation of and ultimate damage to blood vessels, followed by ischemia. Evidence exists, that along with pathogenic involvement of immune-complex-mediated mechanisms in vasculitis syndromes, cell-mediated immune injury may also play a major role. Specifically, vascular endothelial cells secrete IL-1, which may then activate T lymphocytes and promote inflammation within the blood vessel.

Therefore, the present invention also relates to treatment of various vascular syndromes, including but not limited to, polyarteritis nodosa, allergic angiitis, polyangiitis overlap syndrome and giant cell arteritis (temporal arteritis and Takayasu's arteritis). Treatment involves systemic delivery of DNA sequences encoding IL-1 antagonists, as described hereinbefore for treatment of rheumatoid arthritis and systemic lupus erythematosus.

In a further embodiment regarding treatment of vascular syndromes, any of the strategies disclosed within the specification may be utilized for targeting nucleic acid of interest to the appropriate cell type so as to promote expression of the therapeutic agent, including but not necessarily limited to a nucleic acid sequence encoding (1) IRAP or a biologically active fragment thereof; (2) a soluble receptor of IL-1 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid sequence encoding IGF-1 or a biologically active fragment thereof, and TGF-β or a biologically active fragment thereof; and (10) a nucleic acid fragment encoding constituents of the extracellular matrix, such as collagen.

5.4.7. SYSTEMIC TREATMENT OF ANKYLOSING SPONDYLYTIS

Ankylosing spondylytis is a systemic rheumatic disorder characterized by inflammation of the axial skeleton and large peripheral joints. An additional embodiment of the invention indicates treatment of this type of inflammatory arthritis in the same manner as disclosed for rheumatoid arthritis.

As disclosed in embodiments regarding treatment of rheumatoid arthritis, any of these strategies may be utilized for treating ankylosing spondylytis by targeting the nucleic acid of interest to the appropriate cell type so as to promote expression of the therapeutic agent, including but not necessarily limited to a nucleic acid sequence encoding (1) IRAP or a biologically active fragment thereof; (2) a soluble receptor of IL-1 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid sequence encoding IGF-1 or a biologically active fragment thereof, and TGF-62 or a biologically active fragment thereof; and (10) a nucleic acid fragment encoding constituents of the extracellular matrix, such as collagen.

5.4.8. SYSTEMIC TREATMENT OF JUVENILE RHEUMATOID ARTHRITIS

Juvenile rheumatoid arthritis is a form of rheumatoid arthritis which manifests itself prior to age 16. Three subtypes (systemic, pauciarticular and polyarticular) have been designated. The disease tends to affect larger joints that may interfere with growth and development.

This embodiment of the invention dictates use of systemic forms of delivering anti-arthritic proteins or protein fragments as treatment for the disorder. As disclosed above for ankylosing spondylytis, treatment of juvenile rheumatoid arthritis in the same manner as disclosed for rheumatoid arthritis is embraced in the present invention.

As disclosed in embodiments regarding treatment of rheumatoid arthritis, any of these strategies may be utilized for treating juvenile rheumatoid arthritis by targeting the nucleic acid of interest to the appropriate cell type so as to promote expression of the therapeutic agent, including but not necessarily limited to a nucleic acid sequence encoding (1) IRAP or a biologically active fragment thereof; (2) a soluble receptor of IL-1 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid sequence encoding IGF-1 or a biologically active fragment thereof, and TGF-β or a biologically active fragment thereof; and (10) a nucleic acid fragment encoding constituents of the extracellular matrix, such as collagen.

5.4.9. SYSTEMIC TREATMENT OF PSORIATIC ARTHRITIS

Psoriatic arthritis is a rheumatoid-like arthritis associated with psoriasis of the skin or nails. The majority of patients are affected either at two or three joints or in a systemic fashion. Present forms of treatment include NSAIDs or steroid injections to treat inflammation.

Therefore, it is an additional embodiment of the invention to systemically treat patients suffering from psoriatic arthritis in one or more of the therapeutic strategies hereinabove disclosed for rheumatoid arthritis.

As disclosed in embodiments regarding treatment of rheumatoid arthritis, any of these strategies may be utilized for treating psoriatic arthritis by targeting the nucleic acid of interest to the appropriate cell type so as to promote expression of the therapeutic agent, including but not necessarily limited to a nucleic acid sequence encoding (1) IRAP or a biologically active fragment thereof; (2) a soluble receptor of IL-1 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid sequence encoding IGF-1 or a biologically active fragment thereof, and TGF-β or a biologically active fragment thereof; and (10) a nucleic acid fragment encoding constituents of the extracellular matrix, such as collagen.

5.4.10. SYSTEMIC TREATMENT OF OSTEOGENESIS IMPERFECTA

Osteogenesis imperfecta encompasses a group of related hereditary diseases which are characterized by a defect in the synthesis of type I collagen, which constitutes approximately 90% of the bone matrix. The disease is grouped into four subtypes (OI I, OI II, OI III and OI IV), depending on the clinical phenotype. Assembly of collagen fibrils comprises synthesis and triple-helix formation of pro-α chains to form procollagen, which is secreted into the extracellular matrix and proteolytically cleaved to form a collagen molecule. Type I collagen is composed of two types of the α-chain, α-1 and α-2. The mature form of collagen is then assembled into a collagen fibril.

Treatment of osteogenesis imperfecta will encompass either systemic or local delivery of one of both of the α-1 and α-2 collagen genes so as to compensate for the specific OI subtype defect. Any mode of delivery hereinbefore described may be utilized to deliver the gene encoding either α-1 and α-2 or a gene fragment encoding a biologically active fragment thereof.

In a preferred embodiment, the nucleic acid sequence of interest will be ligated to a viral vector such as an MFG based MoMLV retroviral vector, this retroviral vector will be transferred into a standard retroviral packaging cell line and the recovered viral particles used to transfect bone marrow cell populations containing hematopoietic progenitor cells. These in vitro transfected cell populations will then be reintroduced into the circulatory system of the patient as described in Example Section 6.

5.4.11. SYSTEMIC TREATMENT OF OSTEOPOROSIS

Osteoporosis is a disorder characterized by a decrease in bone mass such that the skeleton is rendered fragile and therefore susceptible to fracture. The pathogenesis of the disease is based on increased osteoclastic resorption coupled with decreased bone formation, resulting in the net loss of bone mass. Increases in resorption are promoted by systemic (such as decreases in estrogen and calcitonin and an increase in PTH) and local factors (such as IL-1, IL-6 and TNF-α produced locally by macrophages and osteoclasts).

Therapeutic treatment of osteoporosis includes embodiments regarding treatment of rheumatoid arthritis, including but not necessarily limited to a nucleic acid sequence encoding (1) IRAP or a biologically active fragment thereof; (2) a soluble receptor of IL-1, IL-6 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid encoding IGF-1 or a biologically active fragment thereof, and TGF-β or a biologically active fragment thereof; and (10) a nucleic acid fragment encoding constituents of the extracellular matrix, such as collagen.

Nucleic acid sequences encoding anti-inflammatory therapeutic gene products or biologically active fragments thereof which decrease local concentration of IL-1 and/or TGF-1 are preferred in the treatment of osteoporosis. Delivery of the nucleic acid sequence of interest may include any of the strategies for local or systemic delivery disclosed in this specification, preferably utilizing systemic delivery by way of retroviral mediated infection of either hematopoietic stem cell populations such as bone marrow cells or CD34+ cell populations.

5.4.12. SYSTEMIC TREATMENT OF PAGET'S DISEASE

Paget's disease (Osteitis deformans) is a skeletal disease marked initially by osteoclastic bone resorption which in turn triggers replacement of normal marrow with vascular fibrous connective tissue. Thus, the resorbed bone is replaced by course-fibered, dense trabecular bone arranged in a disordered fashion. Paget's disease may well be caused by a viral infection. Possible causal viral agents are a slow-virus infection by paramyxovirus, measles virus, a respiratory syncytial virus or a canine virus. Thus, it is possible that different viruses may be responsible for Paget's disease in different patients.

Present therapeutic indications include aspirin, NSAIDs and glucocorticoids, calcitonins, cytotoxic drugs such as plicamycin and dactinomycin, and etidronate, a diphosphonate compound.

As disclosed in embodiments regarding treatment of rheumatoid arthritis, any of these strategies may be utilized for treating Paget's disease by targeting the nucleic acid of interest to the appropriate cell type so as to promote expression of the therapeutic agent, including but not necessarily limited to a nucleic acid sequence encoding (1) IRAP or a biologically active fragment thereof; (2) a soluble receptor of IL-1, IL-6 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid sequence encoding IGF-1 or a biologically active fragment thereof, and TGF-β or a biologically active fragment thereof; and (10) a nucleic acid fragment encoding constituents of the extracellular matrix, such as collagen.

Nucleic acid sequences encoding anti-inflammatory therapeutic gene products or biologically active fragments thereof, systemically delivered by way of retroviral mediated infection of either hematopoietic stem cell populations such as bone marrow cells or CD34+ cell populations are preferred in the treatment of Paget's disease.

5.4.13. SYSTEMIC TREATMENT OF INFLAMMATORY BOWEL DISEASE

Inflammatory bowel disease is a generic term relating to a group of chronic inflammatory disorders of unknown etiology involving the gastrointestinal tract. Chronic inflammatory bowel disease is divided into two major groups, ulcerative colitis and Crohn's disease. While the cause of inflammatory bowel disease is unknown, possible etiologic factors include infectious, immunologic, familial or psychological factors. Secondary extraintestinal manifestations such as arthritis and pericholangitis often times occur during chronic inflammatory bowel disease. Drug therapy of inflammatory bowel disease includes administration of anti-inflammatory drugs, sulfasalazine (the active compound thought to be 5-aminosalicylate, most likely by inhibiting prostaglandin synthesis) and glucocorticoids.

Therefore, the present invention relates to systemic therapeutic treatment of inflammatory bowel disease which include embodiments discussed for rheumatoid arthritis, including but not limited to (1) IRAP or a biologically active fragment thereof; (2) a soluble receptor of IL-1 or a biologically active fragment thereof; (3) IL-4 or a biologically active fragment thereof; (4) IL-10 or a biologically active fragment thereof; (5) a soluble receptor of TNF-α or a biologically active fragment thereof; (6) a nucleic acid sequence encoding an inhibitor of metalloproteinases or a biologically active fragment thereof, such as TIMP; (7) a nucleic acid sequence encoding an antiadhesion molecule such as soluble ICAM-1, soluble CD44, soluble CD18 or biologically active fragments of soluble ICAM-1, soluble CD44 or soluble CD18; (8) a nucleic acid sequence encoding an anti-oxidant, such as superoxide dismutase, or a biologically active fragment thereof, and an inhibitor of nitric oxide synthase, or biologically active fragments thereof; (9) a nucleic acid sequence encoding IGF-1 or a biologically active fragment thereof, and TGF-β or a biologically active fragment thereof; and (10) a nucleic acid fragment encoding constituents of the extracellular matrix, such as collagen. Nucleic acid sequences encoding therapeutic gene products or biologically active fragments thereof which act as anti-inflammatory agents are preferred in the treatment of inflammatory bowel disease and can be delivered by any of the strategies disclosed in this specification.

The following examples are offered by way of illustration of the present invention, and not by way of limitation.

6. EXAMPLE: EFFICIENT SYSTEMIC TRANSFER AND PROLONGED EXPRESSION OF MFG-IRAP IN MICE

6.1. MATERIALS AND METHODS

6.1.1. IRAP cDNA ISOLATION AND RETROVIRAL VECTOR CONSTRUCTION

The MFG vector is a simplified MoMVL vector in which the DNA sequences encoding the pol and env proteins have been deleted so as to render it replication defective. Sequences in the gag gene up to base 1035 have been utilized to increase the packaging efficiency of the unspliced transcript. The cDNA encoding the human interleukin-1 receptor antagonist (IRAP) was inserted into the NcoI and BamHI cloning sites of the retroviral vector MFG shown in FIG. 1.

A human monocyte cDNA library, in lambda gt10, was purchased from Clontech (catalog no. HL1036a). The cDNA library was derived from the human monocyte cell line U937, which had been stimulated with 10 nM phorbol 12-myristate 13-acetate for 48 hours before mRNA isolation. The library was screened for IRAP cDNA clones using a 32P-end labelled oligonucleotide encompassing base pairs 309–391(as indicated by Carter, et al., 1990, Nature 344: 633–638[see FIG. 1 at p. 634]). The probe was antisense. Positive clones were plaque purified from agar plates to nitrocellulose filters. Two positive phage clones with EcoRI flanking sites were isolated and subcloned into the EcoRI site of pUC18 and were shown to have identical restriction maps. One of the clones was then sequenced. The 5' end of the positive cDNA was truncated at bp 93 and replaced with 81 bp of nonsense DNA (most likely a cloning artifact). DNA downstream from about bp 110 was also missing. The missing 5' sequences were replaced via two sequential PCR reactions. In the first reaction, the 5' sense primer covered bp 43–199. The 3' antisense primer covered bp 553–577 and added a HindIII site to the 3' end. The product of this reaction was taken for a second PCR reaction using the same 3' primer and a 5' primer covering bp 1–67 which also added a HindIII site to the 5' end. The second PCR product was digested with HindIII, subcloned into pUC18, and sequenced. The resulting IRAP insert had the following structure (as indicated in SEQ ID NOS:3 and 4, and FIG. 2): a 5' HindIII site followed immediately by bp 1 (again, utilizing the numbering of Carter, et al., 1990, Nature 344: 633–638) the entire IRAP coding sequence, 3' flanking DNA from bp 543–577, followed by a 3' HindIII site. This insert was subcloned into the HindIII site of pSV2cat. One of ordinary skill in the art will be aware that any of a multitude of vector molecules, especially DNA plasmid vector molecules with a unique HindIII site, can be substituted for pSV2cat at this stage of the construction of MFG-IRAP. This cDNA for human IRAP (SEQ ID NO:3 as subcloned into pSV2cat) was inserted into MFG by first BamHI-linkering the 3' HindIII site downstream of the stop codon of the IRAP gene, followed by digestion with Pst1 and BamHI. This Pst1 BamHI IRAP fragment was ligated to NcoI/BamHI digested MFG, with the addition of a synthetic oligonucleotide adapter

5'-CATGGAATCTGCA-3' [SEQ ID NO:1]

3'-CTTTAG-5' [SEQ ID NO:2];

from the NcoI site (representing the start site of translation for IRAP [initiating Met underlined) to the Pst1 site (approximately 12 base pairs downstream from the NcoI site) in a three part ligation reaction, resulting in MFG-IRAP (FIG. 1). The initiation codon of IRAP is underlined in SEQ ID NO:1. The resulting plasmid, termed MFG-IRAP, contains the entire coding region of IRAP. This three part ligation involving a synthetic oligo and two DNA fragments is well known by those skilled in the art of cloning. The straight arrow and the crooked arrow in FIG. 1 represent unspliced and spliced messenger RNAs respectively. IRAP is encoded by the spliced message.

6.1.2. ISOLATION OF VIRUS PRODUCING CELLS

The retrovirus vector carrying the IRAP gene (MFG-IRAP) is cotransfected into the CRIP cell packaging line (Danos and Mulligan, 1988. Proc. Natl. Acad. Sci. USA 85: 6460–6464) with pSVneo (conferring neomycin resistance) into NIH 3T3 cells using a standard $CaPO_4$ transfection procedure. NIH 3T3 transfected cells are selected on the basis of resistance to the antibiotic G418. The viral vector containing the neomycin resistant (neo-r) gene is capable of imparting resistance of the cell line to G418. The CRIP cell line expresses the three viral proteins required for packaging the vector viral RNAs into infectious particles. Moreover, the viral particles produced by the CRIP cell line are able to efficiently infect a wide variety of mammalian cell types including human cells. All retroviral particles produced by this cell line are defective for replication but retain the ability to stably integrate into mammalian cells, thereby becoming an heritable trait of these cells. Virus stocks produced by this method are substantially free of contaminating helper-virus particles and are also non-pathogenic.

6.1.3. COCULTURE WITH HEMATOPOIETIC STEM CELLS

Bone marrow cells were harvested and cocultured with MFG-IRAP containing viral produced cells essentially as described in Ohashi, et al. (Proc. Natl. Acad. Sci. USA 89: 11332–11336). Briefly, bone marrow cells were harvested from limbs of C57 BL/6J-Gpi-1$^a$-Gpi-1a-Hbbd-Hbbd female mice 3 days after injection with 5-fluorouracil (150 mg/kg of body weight). Bone marrow cells were precultured for 2 days in Fischer's medium supplemented with 15% fetal calf serum, 2 mM L-glutamine, 100 units of penicillin per ml, 100 grams of streptomycin per ml, and cytokines. Recombinant rat stem cell factor (Amgen Biologicals) was used in both preculture and coculture at 100 ng/ml. The concentration of cytokines was 100 units of IL-3 and 100 ng of recombinant IL-6. Preculture was followed by 2 days of coculture with 20 Gy-irradiated viral producer cells in DMEM supplemented with 10% calf serum, antibiotics, Polybrene (8 μg/ml) and cytokines. After coculture, lethally irradiated (9.5Gy)B6-(Gpi-1$^b$)/(Gpi-1$^b$) mice were injected with $2 \times 10^6$ bone marrow cells for long-term hematopoietic reconstitution studies.

The techniques described in the previous paragraph were utilized to transfer the E. coliLacZ (β-galactosidase) gene to the bone marrow of mice for use as controls. The LacZ gene was inserted at the viral gag gene and the neomycin-resistance gene, neo, resulting in BAG (FIG. 1).

6.1.4. ASSAY FOR IRAP ACTIVITY IN HEMATOPOIETIC RECONSTITUTED MICE

IRAP activity in reconstituted mice was determined by a human IRAP immunoassay (a quantitative sandwich ELISA) following the manufacturers directions (marketed by Research & Diagnostic Systems, Minneapolis, Minn; under the trademark Quantikine).

6.2. RESULTS

Table 1 shows the results of four separate long-term hematopoietic reconstitution experiments in mice. In all cases, high levels of IRAP expression were obtained. Furthermore, these levels of expression were maintained for at least 13 months. Therefore, these studies provide evidence for the ability to generate a prolonged availability of an IL-1 antagonist in a systemic manner in a mammalian host.

As depicted in Table 2, four IRAP+ mice and four control mice (LacZ+) were injected subcutaneously with long of human recombinant IL-1β. Three hours later, the mice were bled and sera analyzed for the presence of murine IL-6 using a commercial ELISA kit (Endogen, Boston, Mass.). In the control mice, IL-1β induced a large increase in serum IL-6 (from 20 pg/ml in mice injected with saline to 28,721±11,090 pg/ml in LacZ+mice). In the IRAP+ mice, IL-6 levels only reached 8,553±3,785 pg/ml, an inhibition of 70% ($p<0.05$). These data demonstrate that the human IRAP produced systemically in the mice by the disclosed methods is biologically active and able to suppress an IL-1 induced biological response.

As discussed hereinbefore, other IL-1 antagonists, viral or non-viral strategies for preparing the nucleic acid sequence of interest, and modes of systemic delivery to the mammalian host may be utilized to practice the disclosed invention. Therefore, whereas particular embodiments of this invention have been described above for purposes of illustration, it will be evident to those persons skilled in the art that numerous variations of the details of the present invention may be made without departing from the invention as defined in the appended claims.

TABLE 1

| Expt. # | Post Transplant Time (Months) | Number | Serum IRAP (ng/ml + S.D.) |
| --- | --- | --- | --- |
| I | 2 | 10 | 104 ± 13.5 |
| II | 1 | 5 | 513 ± 280.6 |
| III | 3.5 | 5 | 154 ± 111.3 |
| IV | 2 | 7 | 381 ± 80.5 |
|  | 3 | 7 | 306 ± 65.7 |
|  | 4 | 7 | 175 ± 27.7 |
|  | 5 | 7 | 271 ± 59 |
|  | 7 | 7 | 583 ± 247 |
|  | 13 | 7 | 470 ± 165.6 |

TABLE 2

| | | Serum IL-6 (pg/ml) | |
| --- | --- | --- | --- |
| Injection | Mouse # | LacZ$^+$ | IRAP$^+$ |
| carrier |  | 20 | 20 |
| 10 ng IL-1β | 1 | 33,102 | 6,505 |
| 10 ng IL-1β | 2 | 18,859 | 14,125 |
| 10 ng IL-1β | 3 | 42,358 | 7,662 |
| 10 ng IL-1β | 4 | 20,562 | 5,920 |
|  |  | 28,721 ± 11,090 | 8,553 ± 3,785 |

What is claimed is:

1. A method of treating rheumatoid arthritis inflammation in a mammalian host which comprises:

generating a recombinant retroviral expression vector the contains a polynucleotide sequence encoding a biologically active interleukin-1 receptor antagonist protein operatively linked to a promoter that is active in bone marrow cells;

infecting, ex vivo, a population of bone marrow cells from said mammalian host with said vector such that said bone marrow cells express said biologically active interleukin-1 receptor antagonist protein;

injecting said infected bone marrow cells into said host such that systemic transfer and expression of said biologically active interleukin-1 receptor antagonist protein occurs within said host;

wherein said transfer and expression within said host reduces inflammation resulting from rheumatoid arthritis.

2. The method of claim 1 wherein said bone marrow cells comprise $CD34^+$ leukocytes.

3. The method of claim 1 wherein said retroviral vector is MFG-IRAP.

* * * * *